US010478173B2

(12) United States Patent
Oren et al.

(10) Patent No.: US 10,478,173 B2
(45) Date of Patent: Nov. 19, 2019

(54) MEDICAL APPARATUS AND METHOD FOR ATTACHING A SUTURE TO A BONE

(75) Inventors: Ran Oren, Doar-Na Oshrat (IL); Sumant G. Krishnan, Dallas, TX (US); Lee Ranon, Nahariya (IL); Shai Nachmias, Nahariya (IL); Aryeh Mirochinik, Akko (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 1234 days.

(21) Appl. No.: 12/919,516

(22) PCT Filed: Oct. 5, 2008

(86) PCT No.: PCT/IL2008/001316
§ 371 (c)(1), (2), (4) Date: Aug. 26, 2010

(87) PCT Pub. No.: WO2009/107121
PCT Pub. Date: Sep. 3, 2009

(65) Prior Publication Data
US 2011/0009867 A1 Jan. 13, 2011

Related U.S. Application Data

(60) Provisional application No. 61/129,394, filed on Jun. 23, 2008, provisional application No. 61/064,333, filed on Feb. 28, 2008.

(51) Int. Cl.
*A61B 17/04* (2006.01)
*A61B 17/17* (2006.01)
(Continued)

(52) U.S. Cl.
CPC ...... *A61B 17/0469* (2013.01); *A61B 17/0401* (2013.01); *A61B 17/0482* (2013.01);
(Continued)

(58) Field of Classification Search
CPC ............ A61B 17/1714; A61B 17/1796; A61B 2017/1778
(Continued)

(56) References Cited

U.S. PATENT DOCUMENTS 268,344 A * 11/1882 Wood ...................... B25B 23/12 81/125
4,557,259 A 12/1985 Wu
(Continued)

FOREIGN PATENT DOCUMENTS

AU 2008351859 10/2008
CN 2593743 12/2003
(Continued)

OTHER PUBLICATIONS

International Preliminary Report on Patentability dated Oct. 3, 2011 From the International Preliminary Examining Authority Re. Application No. PCT/IL2008/001316.
(Continued)

*Primary Examiner* — Zade Coley
*Assistant Examiner* — Amy R Sipp

(57) ABSTRACT

A method of forming a channel in a bone, the method comprising: providing a first bore in the bone; and forming, a second bore in the bone at a predefined angle from said first bore, using said first bore as a reference point for defining the location of the second bore in the bone, wherein the first and second bores intersect in the bone.

35 Claims, 14 Drawing Sheets

(51) Int. Cl.

| | |
|---|---|
| *A61B 17/16* | (2006.01) |
| *A61B 17/00* | (2006.01) |

(52) U.S. Cl.

CPC ...... *A61B 17/0485* (2013.01); *A61B 17/1684* (2013.01); *A61B 17/1778* (2016.11); *A61B 17/1796* (2013.01); *A61B 2017/00358* (2013.01); *A61B 2017/00424* (2013.01); *A61B 2017/0409* (2013.01); *A61B 2017/0445* (2013.01)

(58) Field of Classification Search

USPC ......... 606/74, 80, 87, 96, 98, 103, 144, 148; 623/13.14

See application file for complete search history.

(56) References Cited

U.S. PATENT DOCUMENTS

| | | | | |
|---|---|---|---|---|
| 5,059,201 | A * | 10/1991 | Asnis | A61B 17/04 606/139 |
| 5,250,055 | A | 10/1993 | Moore et al. | |
| 5,437,677 | A | 8/1995 | Shearer et al. | |
| 5,458,602 | A * | 10/1995 | Goble | A61B 17/1714 606/96 |
| 5,584,839 | A | 12/1996 | Gieringer | |
| 5,681,333 | A | 10/1997 | Burkhart et al. | |
| 5,688,284 | A | 11/1997 | Chervitz et al. | |
| 5,817,110 | A | 10/1998 | Kronner | |
| 6,156,056 | A | 12/2000 | Kearns et al. | |
| 6,443,963 | B1 | 9/2002 | Baldwin et al. | |
| 6,514,258 | B1 * | 2/2003 | Brown | A61C 1/084 408/202 |
| 7,201,756 | B2 | 4/2007 | Ross et al. | |
| 2001/0016747 | A1 * | 8/2001 | Romano | A61B 17/0483 606/148 |
| 2002/0068949 | A1 | 6/2002 | Williamson, IV et al. | |
| 2003/0120287 | A1 * | 6/2003 | Gross | A61B 17/0467 606/148 |
| 2003/0195529 | A1 | 10/2003 | Takamoto et al. | |
| 2004/0254585 | A1 | 12/2004 | Whittaker et al. | |
| 2004/0267273 | A1 | 12/2004 | Whittaker et al. | |
| 2005/0021055 | A1 * | 1/2005 | Toubia et al. | 606/144 |
| 2006/0069399 | A1 | 3/2006 | Weisel et al. | |
| 2006/0241619 | A1 | 10/2006 | Cerundolo | |
| 2006/0241620 | A1 | 10/2006 | Cerundolo | |
| 2006/0241657 | A1 * | 10/2006 | Cerundolo | A61B 17/0401 606/148 |
| 2007/0005067 | A1 * | 1/2007 | Dross | 606/72 |
| 2007/0088362 | A1 | 4/2007 | Bonutti et al. | |
| 2007/0276395 | A1 | 11/2007 | Burn | |
| 2009/0018554 | A1 * | 1/2009 | Thorne | A61B 17/0485 606/145 |
| 2009/0088781 | A1 * | 4/2009 | Prestel | A61B 17/0469 606/148 |
| 2016/0000424 | A1 | 1/2016 | Oren et al. | |
| 2018/0036001 | A1 | 2/2018 | Oren et al. | |

FOREIGN PATENT DOCUMENTS

| | | |
|---|---|---|
| JP | 2007-534380 | 11/2007 |
| JP | 2008-536626 | 9/2008 |
| JP | 2011-512937 | 4/2011 |
| JP | 2013-240614 | 12/2013 |
| RU | 415008 | 7/1974 |
| WO | WO 2005/122921 | 12/2005 |
| WO | WO 2007/002432 | 1/2007 |
| WO | WO 2007/024282 | 3/2007 |
| WO | WO 2007/111986 | 10/2007 |
| WO | WO 2008/015670 | 2/2008 |
| WO | WO 2009/107121 | 9/2009 |

OTHER PUBLICATIONS

Translation of Reason for Rejection dated Jan. 25, 2013 From the Japanese Patent Office Re. Application No. 2010-548242.

Translation of Office Action dated Mar. 4, 2013 From the State Intellectual Property Office of the People's Republic of China Re. Application No. 200880127586.0.

Translation of Search Report dated Mar. 4, 2013 From the State Intellectual Property Office of the People's Republic of China Re. Application No. 200880127586.0.

Response dated Apr. 14, 2011 to Official Action dated Dec. 23, 2010 From the ROSPATENT, Federal Government Institution 'Federal Institute of Industrial Property of the Federal Service for Intellectual Property, Patents and Trademarks' of the Russian Federation Re. Application No. 2020125530.

Patent Examination Report dated May 22, 2013 From the Australian Government, IP Australia Re. Application No. 2008351859.

Quiery for Examination dated May 29, 2912 From the ROSPATENT, Federal Government Institution 'Federal Institute of Industrial Property of the Federal Service for Intellectual Property, Patents and Trademarks' of the Russian Federation Re. Application No. 2020125530 and Its Summary in English.

Translation of Office Action dated Jun. 20, 2012 From the State Intellectual Property Office of the People's Republic of China Re. Application No. 200880127586.0.

International Search Report Dated Feb. 20, 2009 From the International Searching Authority Re.: Application No. PCT/IL2008/001316.

Written Opinion dated Feb. 20, 2009 From the International Searching Authority Re.: Application No. PCT/IL2008/001316.

International Preliminary Report on Patentability dated Sep. 10, 2010 From the International Bureau of WIPO Re. Application No. PCT/IL2008/001316.

Translation of Office Action dated Jan. 29, 2012 From the State Intellectual Property Office of the People's Republic of China Re. Application No. 200880127586.0.

Official Action dated Dec. 23, 2010 From the ROSPATENT, Federal Government Institution 'Federal Institute of Industrial Property of the Federal Service for Intellectual Property, Patents and Trademarks' of the Russian Federation Re. Application No. 2020125530.

Translation of Office Action dated Aug. 22, 2013 From the State Intellectual Property Office of the People's Republic of China Re. Application No. 200880127586.0.

Office Action dated Jun. 22, 2014 From the Israel Patent Office Re. Application No. 206833 and Its Translation Into English.

Examination Report dated May 15, 2014 From the Instituto Mexicano de la Propiedad Industrial Re. Application No. MX/a/2010/009000 and Its Translation Into English.

Notice of Reason for Rejection dated May 23, 2014 From the Japanese Patent Office Re. Application No. 2013-145352 and Its Translation Into English.

Requisition by the Examiner Dated Sep. 16, 2014 From the Canadian Intellectual Property Office Re. Application No. 2,711,430.

Examination Report dated Feb. 24, 2014 From the Instituto Mexicano de la Propiedad Industrial Re. Application No. MX/a/2010/009000 and Its Translation Into English.

Office Action dated Apr. 15, 2014 From the State Intellectual Property Office of the People's Republic of China Re. Application No. 200880127586.0 and Its Translation Into English.

Search Report dated Apr. 15, 2014 From the State Intellectual Property Office of the People's Republic of China Re. Application No. 200880127586.0 and its Translation Into English.

Patent Examination Report dated Feb. 27, 2015 From the Australian Government, IP Australia Re. Application No. 2014201225.

Communication Pursuant to Rule 164(1) EPC [Supplementary Partial European Search Report] dated Jun. 17, 2015 From the European Patent Office Re. Application No. 08808114.6.

Requisition by the Examiner dated Jul. 8, 2015 From the Canadian Intellectual Property Office Re. Application No. 2,711,430.

European Search Report and the European Search Opinion dated Oct. 9, 2015 From the European Patent Office Re. Application No. 15167254.0.

Supplementary European Search Report dated Sep. 10, 2015 From the European Patent Office Re. Application No. 08808114.6.

(56) References Cited

OTHER PUBLICATIONS

Communication Pursuant to Article 94(3) EPC dated Jun. 1, 2016 From the European Patent Office Re. Application No. 08808114.6.
Restriction Official Action dated Jun. 14, 2016 From the U.S. Patent and Trademark Office Re. U.S. Appl. No. 14/856,676.
Notice of Reason for Rejection dated Jan. 12, 2016 From the Japanese Patent Office Re. Application No. 2015-39751 and Its Translation Into English.
Notice of Reason for Rejection dated Aug. 2, 2016 From the Japanese Patent Office Re. Application No. 2015-039751 and Its Translation Into English.
Official Action dated Aug. 26, 2016 From the U.S. Patent and Trademark Office Re. U.S. Appl. No. 14/856,676.
Communication Pursuant to Article 94(3) EPC dated Nov. 9, 2016 From the European Patent Office Re. Application No. 08808114.6. (4 Pages).
Examination Report dated Apr. 3, 2019 From the Serviço Publico Federal, Ministerio da Economia, Instituto Nacional da Propriedade Industrial do Brazil Re. Application No. PI 0820149-8 and Its Summary in English. (6 Pages).
Examination Report dated Nov. 13, 2018 From the Serviço Publico Federal, Ministerio da Industria, Comercio Exterior e Serviços, Instituto Nacional da Propriedade Industrial do Brazil Re. Application No. PI 0820149-8 and Its Summary in English. (8 Pages).
Examination Report dated Mar. 15, 2018 From the Australian Government, IP Australia Re. Application No. 2015255260. (4 Pages).
Examination Report dated Sep. 26, 2017 From the Australian Government, IP Australia Re. Application No. 2015255260. (7 Pages).
Examination Report Under Sections 12 & 13 of the Patents Act, 1970 and the Patents Rules, 2003 dated Dec. 26, 2017 From the Government of India, Intellectual Property Office, Patents, Designs, Trade Marks Geographical Indications Re. Application No. 1337/MUMNP/2010. (8 Pages).
Notice of Reason for Rejection dated Dec. 12, 2017 From the Japan Patent Office Re. Application No. 2017-031851 and Its Translation Into English. (9 Pages).
Office Action dated Apr. 24, 2018 From the Israel Patent Office Re. Application No. 243677 and Its Translation Into English. (6 Pages).
Official Action dated Jan. 11, 2017 From the U.S. Patent and Trademark Office Re. U.S. Appl. No. 14/856,676. (32 pages).
Official Action dated Apr. 23, 2018 From the U.S. Patent and Trademark Office Re. U.S. Appl. No. 14/485,879. (14 pages).
Official Action dated Oct. 25, 2017 From the U.S. Patent and Trademark Office Re. U.S. Appl. No. 14/485,879. (35 pages).
Restriction Official Action dated Jul. 17, 2017 From the U.S. Patent and Trademark Office Re. U.S. Appl. No. 14/485,879. (10 pages).

* cited by examiner

V
VIII
20
20a
21
22
24
25
26
26a
26b
27
27a
28
28a
28b
30
35a
35b
35d
35e
35f 55
55a
55b
55c
55d
56
56a
56b
56c

MEDICAL APPARATUS AND METHOD FOR ATTACHING A SUTURE TO A BONE

RELATED APPLICATIONS

This Application is a National Phase of PCT Patent Application No. PCT/IL2008/001316 having International filing date of Oct. 5, 2008, which claims the benefit of U.S. Provisional Patent Application No. 61/064,333 filed on Feb. 28, 2008 and U.S. Provisional Patent Application No. 61/129,394 filed on Jun. 23, 2008. The contents of the above Applications are all incorporated herein by reference.

FIELD AND BACKGROUND OF THE INVENTION

The present invention relates to medical apparatus, particularly to a medical implement and a kit including such an implement, and also to a method, for attaching a suture to a bone. The invention is especially useful in an arthroscopic surgical procedure for attaching a tendon of a rotator cuff muscle to the humerus bone for repairing a damaged shoulder joint, and is therefore described below with respect to such a procedure.

While the shoulder joint has a great range of motion, it is not very stable. Four rotator cuff muscles (supraspinatus, infraspinatus, subscapularis and teres minor) surround the shoulder joint and provide the power to lift and rotate the arm while keeping the head of the upper arm bone (humerus) in approximation to the socket in the shoulder blade (glenoid) for stability. Each of these muscles is attached by a tendon to the humerus bone. The supraspinatus muscle is attached by the supraspinatus tendon to the superior aspect of the greater tubercle. The infraspinatus muscle is attached by the infraspinatus tendon to the posterolateral aspect of the greater tubercle. The teres minor muscle is attached by the teres minor tendon to the lower aspect of the greater tubercle. The subscapularis muscle is attached by the subscapularis tendon to the lesser tubercle. As one ages, these muscles and tendons become thinner and prone to rupture. A rotator cuff tear may develop gradually or may result suddenly from a single traumatic event. In a younger patient, rupture is usually associated with significant trauma. Rotator cuff tears are tears of one or more of the four tendons of the rotator cuff muscles listed above. Tears of the supraspinatus tendon are the most common, most often involving detachment of the tendon from the bone. The tear of the supraspinatus tendon usually occurs at its point of insertion onto the humeral head at the greater tubercle. Since this tear is the most common, the following description will refer to the supraspinatus tear. However, it is submitted that the invention described below is applicable to any of the rotator cuff tears and in fact to any tear of a tendon from a bone.

When surgical intervention is indicated to repair a rotator cuff tear, the procedure can be performed as an open surgical procedure, or as a minimally invasive (arthroscopic) surgical procedure. Both procedures aim to re-attach the tendon to the bone over an area extending from the anatomical neck to the lateral surface of the tubercle. The relatively large area of attachment is desirable for strengthening purposes and for assisting recovery and healing. This procedure of osseointegration of the tendon to the bone causes bony tissue to be formed around the tendon and anchors it in place.

In open surgery, after the joint has been exposed, the tubercle is accessed laterally, and a row of holes are drilled aiming to exit in the area of the anatomical neck. Sutures are led through these holes; the tendon is stretched to lie over the planned area of attachment; and the suture coming from the exit point is passed through the tendon. When the sutures leading from the inlet and exit points are knotted, one strand overlies the tendon, thus achieving attachment over the surface of the tubercle from the lateral inlets to the anatomical neck.

In contrast, the arthroscopic procedures use bone anchors. Two rows of anchors are implanted, one in the neck area and one on the lateral surface of the tubercle. Sutures leading from the anchors are passed through the tendon and are knotted over it.

Both procedures have shortcomings. With the open method, the bone tunnels for the sutures can be drilled only in one direction, from the lateral upwardly to the anatomical neck. Access for drilling from the anatomical neck at an angle to reach the side of the tubercle is obstructed by the patient's neck and head. It is difficult to achieve exactly the desired exit points for the drill. Exiting on the spherical humeral head must be avoided. Drilling at a more acute angle for safety may result in being too close to the surface of the tubercle.

A minimally invasive (arthroscopic) method is desirable when not contra-indicated from medical considerations. However, the conventional arthroscopic procedure uses anchors resulting in points or lines of attachment, rather than in attachments over a significant surface.

OBJECTS AND BRIEF SUMMARY OF THE PRESENT INVENTION

Objects of the present invention are to provide a medical implement, a kit including such an implement, and a method, for attaching a suture to a bone having advantages in one or more of the above respects and particularly useful in an arthroscopic surgical procedure.

There is thus provided in accordance with an exemplary embodiment of the invention a method of forming a channel in a bone, the method comprising:

providing a first bore in the bone; an forming, a second bore in the bone at a predefined angle from said first bore, using said first bore as a reference point for defining the location of the second bore in the bone, wherein the first and second bores intersect in the bone.

In an exemplary embodiment defining the location further comprises defining the depth of the second bore such that the second bore intersects with the first bore but will not exit the bone except at a single point.

Optionally, using said first bore as a reference point comprises inserting a hook in said first bore. Optionally, said hook and a drill for forming said second bore are linked such that the second bore is at a predetermined angle from the first bore.

Optionally, forming said second bore comprises forming such that the second bore extends past the intersection of the first and second bore in the bone. Optionally, forming said second bore comprises forming such that the second bore does not cross the bone.

In an exemplary embodiment said bone is a humerus bone.

There is further provided in accordance with an exemplary embodiment of the invention, a method of forming a bore in a bone, the method comprising:

providing a first bore in the bone;

providing an implement comprising a hook having an end portion for insertion in the first bore and a passageway for receiving tools, the passageway being at a non-zero angle to the portion;

inserting the hook in the first bore;

clamping the implement to the bone using the hook as an arm of the clamp;

forming a second bore using a drill inserted through said passageway in the implement, such that the first and second bore intersect in the bone.

In an exemplary embodiment, said implement further comprises a locking mechanism for clamping the implement to the bone. Optionally, forming a second bore comprises forming a second bore extending past the intersection of the first and second bore in the bone. Optionally, forming a second bore comprises forming a second bore which does not exit the bone at more than one point.

In an exemplary embodiment, said bone is a humerus bone.

There is further provided in accordance with an exemplary embodiment of the invention, a method of attaching a suture to a bone, the method comprising:

providing a first and second bore in a bone, the first and second bores intersecting in the bone;

providing a suture having a first and second end;

threading the first end of a suture through the second bore, while leaving the second end outside the bone;

capturing the first end of the suture from the first bore at the intersection of the bores in the bone; and threading the first end of the suture through the first bore.

Optionally, said suture is also threaded through a tendon. Optionally, the method further comprises knotting the first and second ends of the suture.

In an exemplary embodiment, said bone is a humerus bone.

There is further provided in accordance with an exemplary embodiment of the invention, a medical implement for forming a bore in a bone, comprising:

a hook for inserting in a first bore in a bone;

a passageway for receiving tools;

wherein said passageway is adapted for receiving a drill for forming a second bore in a bone when said hook is inserted in the first bore, and wherein the second bore is oriented with respect to the hook such that said second bore intersects with the first bore in the bone.

Preferably, the second bore is oriented with respect to the hook such that the first bore and second bore define a predefined angle.

Optionally, said drill comprises a stop adapted to define the depth of the second bore to be formed. Optionally, said implement further comprises a locking mechanism for clamping the implement to the bone.

In an exemplary embodiment, said locking mechanism consists of a first and a second element which clamp the bone between them and wherein said first element is the hook inserted into the first bore. Preferably, said predefined angle is 70°. Optionally, said predefined angle is between 65° and 75°.

There is further provided in accordance with an exemplary embodiment of the invention, a medical implement for forming a bore in a bone, comprising:

a hook for inserting in a first bore in a bone; and a passageway for placement at an entrance to a second bore in the bone, wherein said hook comprises a loop extending thereform, said loop being adapted to grasp an end of a suture inserted through the passageway and through the second bore.

Optionally, said hook is further adapted to extract the suture through the first bore. Optionally, said implement further comprises a locking mechanism for clamping the passageway against the bone when the hook is inserted into the first hole.

There is further provided in accordance with an exemplary embodiment of the invention, a medical implement for forming a bore in a bone, the implement comprising:

a hook for inserting in a first bore in a bone;

a passageway for placement at an entrance to a second bore in the bone; and a locking mechanism for clamping the passageway against the bone, wherein said locking mechanism consists of a first and a second element which clamp the bone between them and wherein said first element is the hook inserted into the first bore.

There is further provided in accordance with an exemplary embodiment of the invention a medical kit of instruments for forming a bore in a bone, comprising:

a first drill for drilling a first bore in a bone;

a second drill for drilling a second bore in the bone;

a suture for threading through said first and second bores in the bone; and a medical implement according to exemplary embodiments of the present invention.

Optionally, said kit further comprises: a drill guide for receiving said first drill and forming said first bore.

In an exemplary embodiment said second drill is thinner then said first drill.

Optionally, said first and second drills comprise a stop such that said first bore formed with said drill does not pass through the bone.

Optionally, said kit further comprises a suture loader for threading said suture through said second bore.

According to one aspect of the invention, there is provided a medical implement for attaching suture to a bone, particularly useful in arthroscopic surgical procedures, comprising a handle having a proximal end for manual grasping and a distal end for engagement with a bone to which a suture is to be attached, the bone being pre-formed with a first bore for receiving one end of the suture; a hook carried at the distal end of the handle, spaced from an outer surface at the distal end of the handle, and configured for reception in the first bore of the bone; the hook or distal end of the handle being in the form of a movable member movable to an extended position with respect to the other to facilitate reception of the hook into the first bore, and to a retracted position with respect to the distal end of the handle for clamping the handle to the bone at a predetermined angle with respect to the first bore; and a manually manipulatable member carried by the proximal end of the handle and coupled to the movable member for moving the movable member to the extended and retracted positions; the handle being formed with a passageway extending longitudinally therethrough from its proximal end to its distal end, the passageway being configured for receiving a drill, after the handle has been clamped to the bone, for drilling a second bore through the bone at the predetermined angle with respect to the first bore and, after the drill has been removed from the passageway, for passing through the passageway the one end of the suture to traverse, and to extend past, the first bore such that the one end of the suture is accessible through the first bore for being pulled out therefrom, while the opposite end of the suture is accessible through the second bore for pulling out therefrom in order to attach the suture to the bone.

Two embodiments of the invention are described below for purposes of example. In one described embodiment, the movable member is the hook, and is movable to its extended and retracted positions with respect to the distal end of the handle. In a second described embodiment, the movable member is the distal end of the handle, which is movable to its extended and retracted positions with respect to the hook.

In both described preferred embodiments, the hook includes a loop movable to an extended position with respect to the hook for facilitating entry of the first end of the suture through the loop into the first bore of the bone, and to a retracted position towards the hook for clamping the first end of the suture to enable pulling-out the first end of the suture through the first bore of the bone. In addition, the handle includes a second manually manipulatable member carried by the proximal end of the handle and coupled to the handle for moving the loop to its extended and retracted positions.

In another described embodiment, the first end of the suture is accessed through the first bore in the bone, and pulled out, by a suture hook.

According to another aspect of the present invention, there is provided a medical kit useful for attaching a suture to a bone, the kit including a medical implement as described above, and a drill receivable within the passageway of the handle for drilling the second bore in the bone; the drill including a stop engageable with the proximal end of the handle to fix the length of the second bore to extend for a slight distance past the first bore, to thereby permit the first end of the suture to traverse and extend past the first bore in order to facilitate its access and extraction via the first bore.

According to a still further aspect of the present invention, there is provided a method for attaching a suture to a bone particularly in an arthroscopic procedure, comprising: forming a first bore in the bone; forming a second bore in the bone intersecting the first bore and extending at a predetermined angle thereto; introducing into the second bore a first end of a suture to extend through the second bore past the intersection of the second bore with the first bore, with the opposite end of the suture extending outwardly of the second bore; accessing the first end of the suture via the first bore; and extracting the first end of the suture via the first bore, to enable attaching the suture to the bone via the end of the suture.

As will be described more particularly below, the invention enables the surgeon to perform bone tunnels in the bone in exactly the required locations to receive sutures, and thereby to achieve reattachment of the torn tendon without the use of bone anchors, in a manner similar to that of the open surgical procedure. The invention is therefore particularly useful in an arthroscopic surgical procedure, but may also be used in an open surgical procedure.

Further features and advantages of the invention will be apparent from the description below.

BRIEF DESCRIPTION OF THE DRAWINGS

The invention is herein described, by way of example only, with reference to the accompanying drawings, wherein.

Figure 1A:
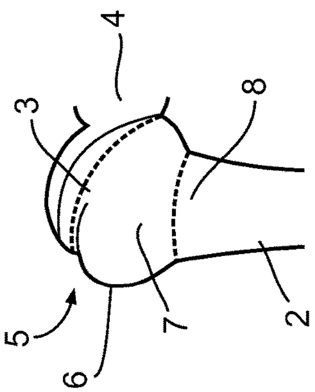
FIGS. 1A, 1B and 1C illustrate the construction of the shoulder joint to be repaired according to an embodiment of the present invention, including the construction of the upper part of the humerus bone (FIG. 1A), a schematic section through the shoulder joint (FIG. 1B), and a damaged shoulder joint (FIG. 1C) to be repaired.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS OF THE INVENTION

An aspect of some embodiments of the invention relates to attaching a tendon to a bone by threading a suture through a channel in the bone and through the tendon. In an exemplary embodiment of the invention, the channel comprises of a first and a second bore intersecting in the bone. In an exemplary embodiment of the invention, the intersection of the bores define a predetermined angle between them, suitable for attaching a tendon to the bone by threading a suture through the bores and the tendon. Preferably, the first and second bores are formed in an arthroscopic procedure.

In an exemplary embodiment, the first bore is formed first and is then used to assist forming the second bore. Optionally, the first bore is used as a reference point for determining the location and/or alignment of the second bore in the bone. Alternatively or additionally, the reference point is used for determining the depth of the second bore such that the first and second bores intersect in the bone. Optionally, at least one of the first and second bore extends past the intersection of the bores in the bone such that a hook or loop may be inserted in one of the bores, crossing the intersection of the bores in the bone, to conveniently capture a suture inserted via the other bore.

In an exemplary embodiment of the invention, a hook inserted into the first bore is used for clamping an implement, with which the second bore is formed, to the bone, thereby stabilizing the implement when drilling the second bore. Optionally, the hook extending from the implement is inserted into the first bore and is used as an arm for the clamp. The implement is then locked in a position clamped to the bone, with the first bore as both a reference and a holding point for the implement. The second bore is then formed by a tool preferably guided by a passageway in the implement. Optionally, the hook has a tip in the form of a rod, inserted in the first bore.

An aspect of some embodiments of the invention relates to threading a suture though the second bore and extracting the suture through the first bore. In an exemplary embodiment of the invention an end of a suture is threaded through the second bore and grasped at the intersection of the bores in the bone by a loop extending from the hook inserted through the first bore. The loop with the suture is then extracted through the first bore. Optionally, said loop is replaced with any other suitable mechanism known in the art for grasping a suture, for example, a hook.

In an exemplary embodiment of the invention there is provided an implement comprising a hook for insertion into a first bore. In an exemplary embodiment, the hook comprises a mechanism configured to grasp an end of a suture threaded through the second bore at the intersection of the bores in the bone. Optionally, the mechanism is further configured to thread the end of the suture through the first bore when extracting the hook from the bore. Optionally, said mechanism comprises a loop. Optionally, the loop is movable between an extracted position in which it is removed from the bore and an extended position in which it is extended into the intersection of the bores to grasp the end of the suture.

In an exemplary embodiment of the invention, the implement comprising a hook further comprises a passageway for receiving tools for forming of or inserting into a second bore. Optionally, the hook and the passageway are located such that when the hook is inserted into the first bore, a drill inserted through the passageway is configured to drill a second bore at a predefined angle from the first bore. Optionally, the predefined angle is 70°. Alternatively, the predefined angle is between 65° and 75°. Alternatively, the predefined angle is between 30° and 120°.

Optionally. The drill is further configured to aid in determining the depth of the second bore to be drilled, by reference to the position of the hook which is inserted in the first bore. In an exemplary embodiment of the invention, the drill is configured such that the depth of the second bore to be drilled is suitable for different bones of a plurality of subjects and does not require adjustment for specific bones.

Optionally, the implement further comprises a locking mechanism for clamping the implement to the bone when the hook is inserted into the first bore.

In an exemplary embodiment, the first and second bores are formed with a same implement comprising of two channels for receiving tools such as a drill and a suture. In this embodiment the two bores are formed at the same side of the bone and the angle formed between the bores is preferably less than 45°.

In the following description reference will be made to attaching a supraspinatus tendon to a humerus bone. However, it is understood that the invention may be adapted to attach any tendon or other soft tissue to any bone of a body.

Figure 1B:
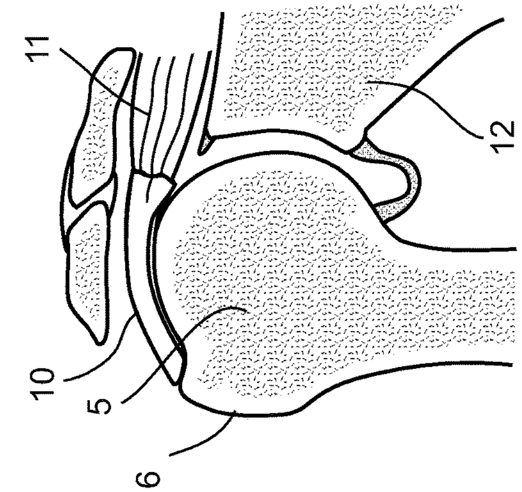
Figure 1C:
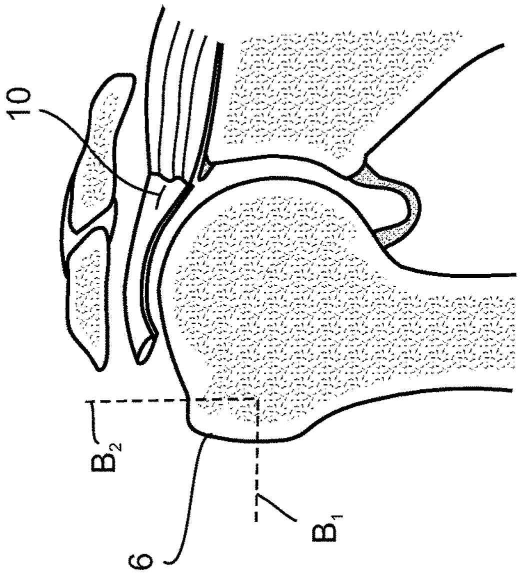

The Shoulder Joint and Its Repair (FIGS. 1A-1C)

FIG. 1A schematically illustrates the structure of the upper part of a humerus bone 2. It includes a spherical head 3 for reception in the glenoid socket 4, and an anatomical neck 5 joined to a greater tubercle 6 and a lesser tubercle 7. The juncture of the latter with the humerus bone 2 is a surgical neck 8.

FIG. 1B is a schematic coronal section through the shoulder joint, showing: a supraspinatus tendon 10 of a supraspinatus muscle 11, the greater tubercle 6, and a shoulder blade (scapula) 12.

FIG. 1C schematically shows the separation of the tendon 10 from the greater tubercle 6 in a damaged shoulder joint which is to be repaired by the reattachment of the tendon.

As will be described below, this is accomplished, according to some embodiments of the present invention, by forming two bores $B_1$ and $B_2$ (FIG. 1C). The tendon is captured and drawn toward the left in the figure, so that it covers bore $B_2$, as described below and a suture or sutures are passed through the two bores and through the tendon 10; and knotting the two ends of the suture or sutures, to thereby firmly attach the tendon to the bone. As will also be described below, the invention enables the two bores $B_1$, $B_2$ to be conveniently made in their required locations and at a predetermined angle to each other to achieve the reattachment of the torn tendon by sutures, rather than by bone anchors, in a manner similar to the open surgical procedures, thereby enabling an arthroscopic surgical procedure to be used for repairing a damaged shoulder joint.

The Medical Implement of FIGS. 2-10D

The medical implement illustrated in FIGS. 2-10D is a bone-tunneling implement according to an embodiment of the invention, designed for use in a medical procedure, particularly an arthroscopic surgical procedure for attaching a suture to a bone, utilizing the two-bore technique of FIG. 1C for receiving the suture through the two bores $B_1$, $B_2$, as briefly described above, and as to be described more particularly below.

Figure 2:
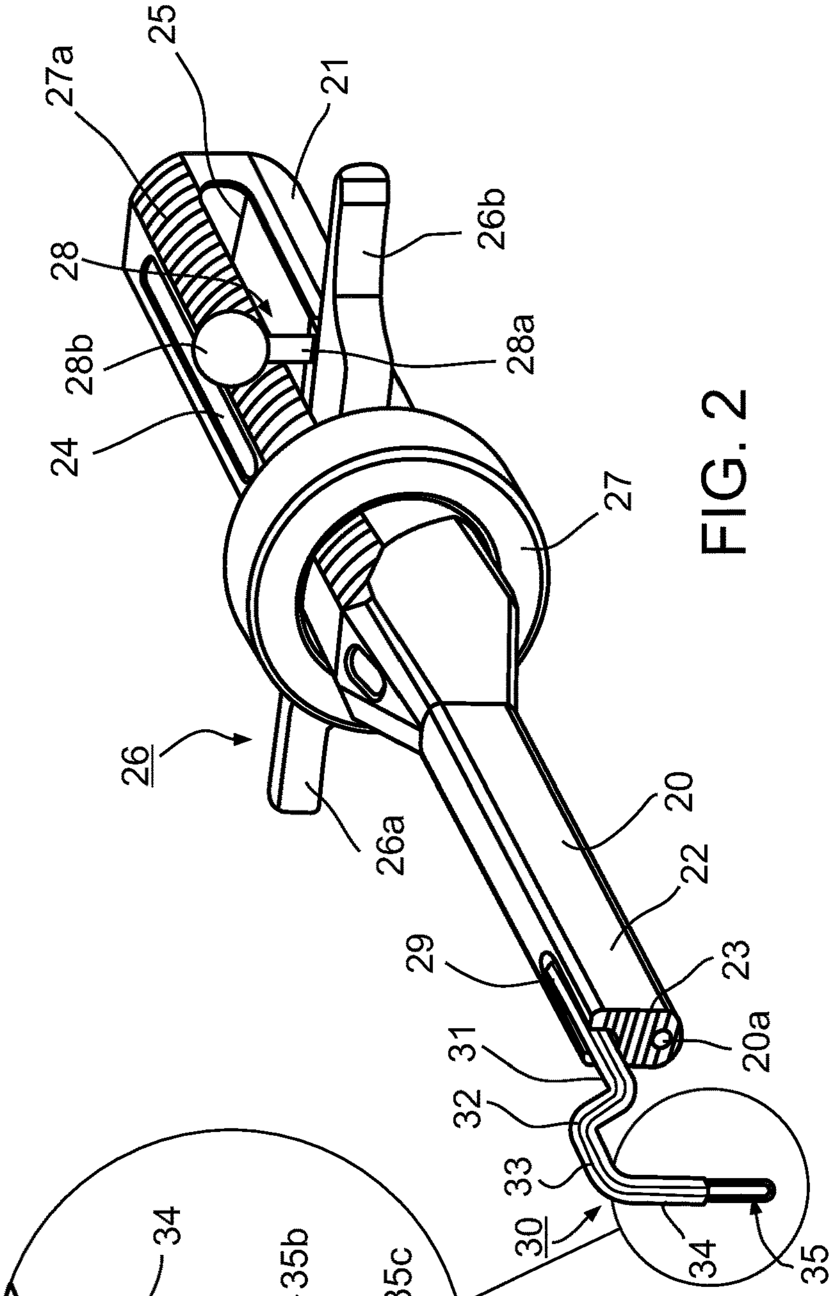
FIG. 2 is a perspective view of one preferred embodiment of a medical bone-tunneling implement constructed according to the present invention for use in repairing a damaged shoulder joint.

FIG. 2 illustrates the medical implement used for producing bore $B_2$ (FIG. 1C) after bore $B_1$ has been formed, so that the two bores are located to intersect each other at a preselected angle for receiving the suture. The implement illustrated in FIG. 2 includes a handle 20 having a proximal end 21 for manual grasping, and a distal end 22 for engagement with the bone to which the suture is to be attached after bore $B_1$ has been formed in the bone. As shown in FIG. 2, the distal end 22 of the illustrated implement is optionally formed with a ribbed outer surface 23 to enable secure engagement with the bone.

Figures 4, 5, 6A, 6B, 7:
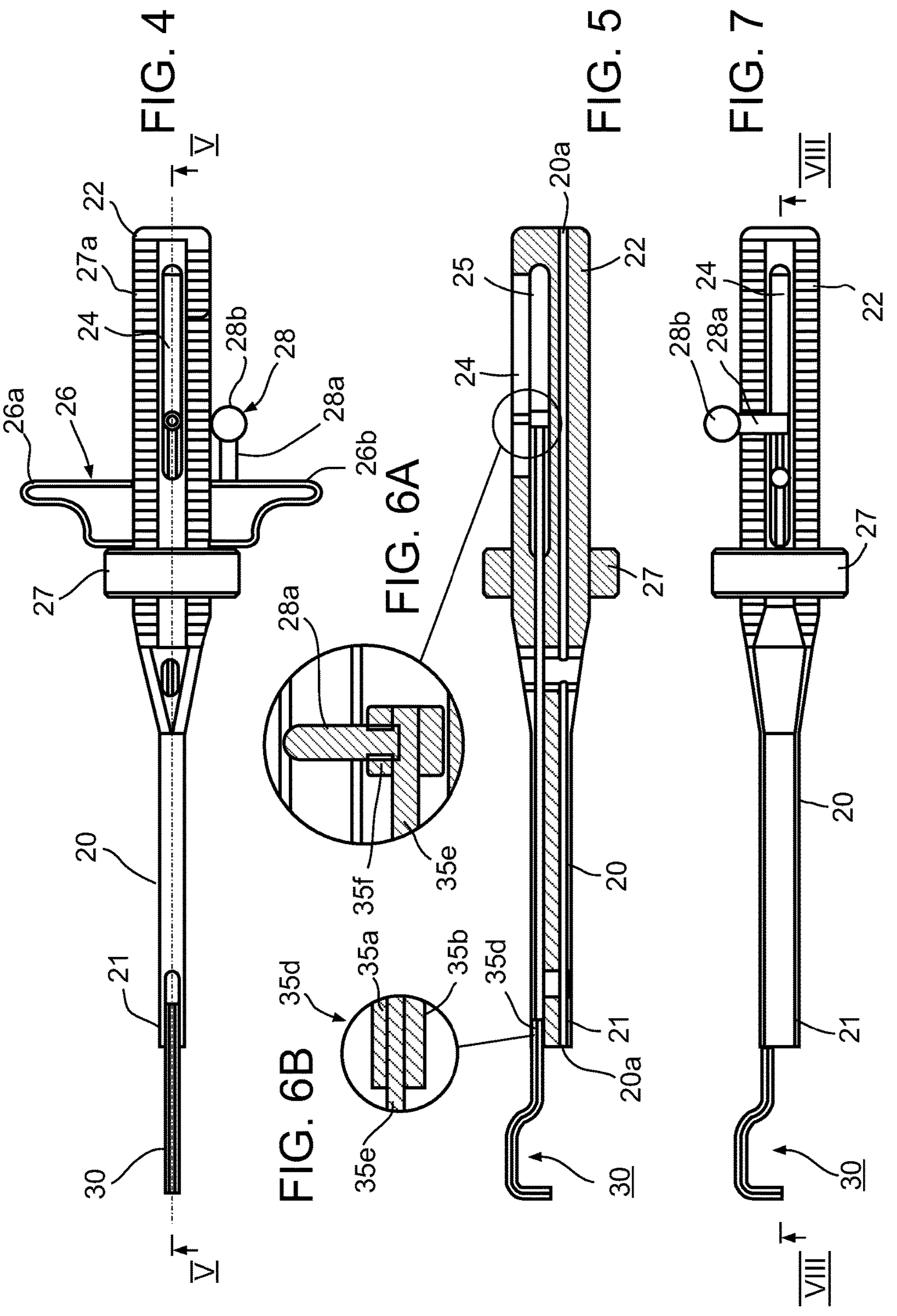
FIG. 4 is a top view of the implement of FIG. 2.
FIG. 5 is a sectional view along line V-V of FIG. 4.
FIGS. 6A and 6B are enlarged fragmentary views of the encircled portions of FIG. 5.
FIG. 7 is a side view of the medical implement of FIG. 2.

Handle 20 is further preferably formed with a passageway 20*a* therethrough extending from the proximal end toward its distal end (FIGS. 2 and 5). As will be described more particularly below, this passageway is located and configured first to receive a drill for making bore $B_2$ (FIG. 1C), and then to receive one end of a suture to be attached to the bone.

The proximal end 21 of the implement illustrated in FIG. 2 is optionally of an octagonal shape. It is further optionally formed with an elongated slot 24 longitudinally of its upper face terminating in a transversely extending slot formed through its two opposed side faces.

The proximal end 21 of handle 20 further carries an optional manually manipulatable member 26 optionally including two opposed finger pieces 26*a*, 26*b* connected by a central stem 26*c* (FIG. 9) located within slots 24 and 25 and movable therealong preferably to the ends of the two slots 24 and 25. The distal end 21 of handle 20 further carries an optional lock nut 27 having internal threads threadedly received on threads 27*a* formed in the side walls in the proximal end 21 of handle 20. As will be described more particularly below, manipulatable member 26 is slidable within slot 25, and lock nut 27 is effective to lock member 26 in its moved position.

The distal end 21 of handle 20 further includes another manipulatable member 28 having a stem 28*a* (FIG. 4) extending through the upper slot 24, and an optional knob 28*b* engageable by the user for moving member 28 to its forward position illustrated in FIG. 2, or to its rearward position at the end of slot 24.

Figures 10A, 10B, 10C, 10D:
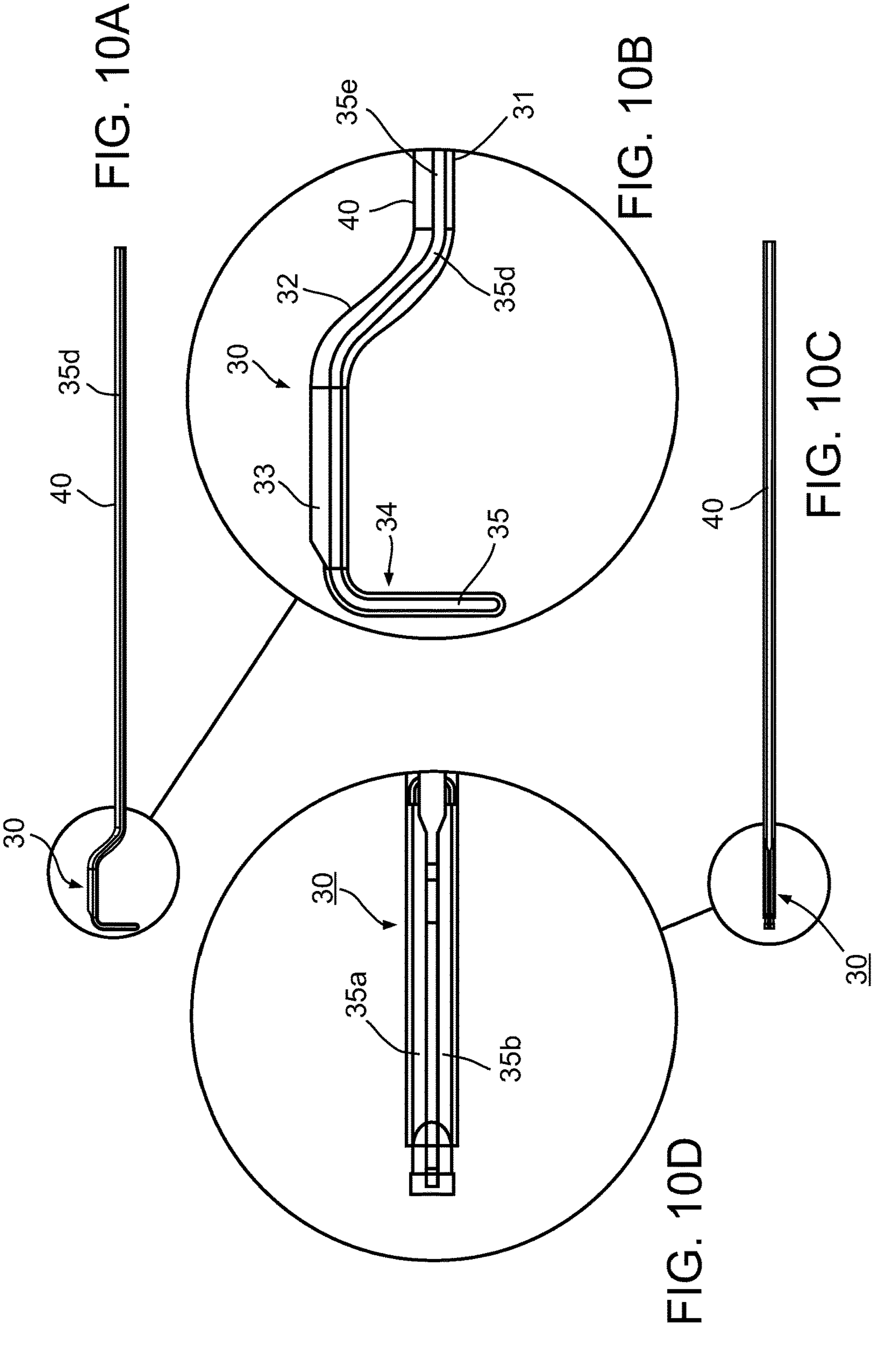
FIGS. 10A-10D are enlarged views of the hook at the distal end of the medical implement of FIG. 2.

The distal end 22 of handle 20 is formed with a slot 29 (FIG. 2) for the reception of a hook, generally designated 30, coupled to manipulatable member 26 so as to be movable from an extended position, illustrated in FIG. 2, to a retracted position towards the ribbed distal outer surface 23 of the handle. Manipulatable member 26 is used for extending hook 30 to its illustrated extended position to facilitate reception of the hook into the first bore $B_1$ (FIG. 1C) of the bone, and to its retracted position for clamping the handle to the bone such that the passageway 20*a*, which is used for making the second bore $B_2$ (FIG. 1C), is at a predetermined angle (in this case) 90° with respect to, and in alignment with, the first bore $B_1$. Optionally, the angle is 70°. Alternatively, the angle is between 65° and 75°. alternatively, the angle is between 30° and 120°. Thus, as shown in FIGS. 2 and 10B, hook 30 includes a first section 31 received within slot 29 of the handle, an upwardly-extending section 32 joined to a horizontal section 33, and a downwardly-extending end section 34 to be received within bore $B_1$, as shown in FIG. 23.

Figure 3:
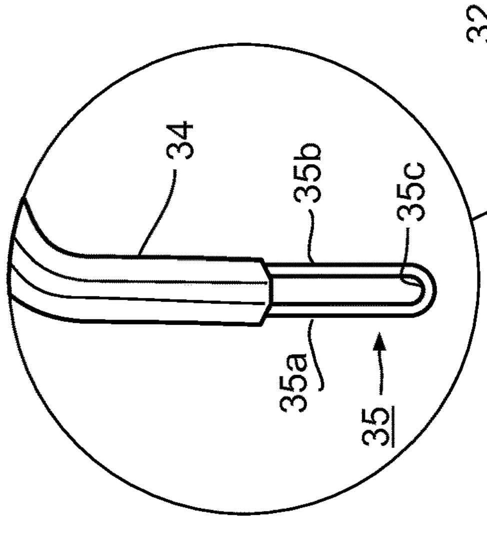
FIG. 3 is an enlarged detailed view of the distal end of the medical implement of FIG. 2, and particularly the loop projecting from the hook at the distal end.

A loop 35 is optionally received within the downwardly-extending end section 34 of hook 30. It includes a pair of parallel legs 35*a*, 35*b* (FIGS. 3 and 10D) joined by a bridging section 35*c*. As will be described more particularly below, hook 35 is coupled to manipulatable member 28. Manipulatable member moves the hook to an extended position, as illustrated in FIGS. 2 and 3 or to a retracted position towards the tip of the downwardly-extending section 34 of hook 30. The position of the hook in the extended position enables a suture to pass between the two legs 35*a*, 35*b*. Optionally, the hook is then moved to a retracted position for extraction from bore $B_1$ (FIG. 1C) of the bone to which the suture is to be attached.

Figures 8, 9:
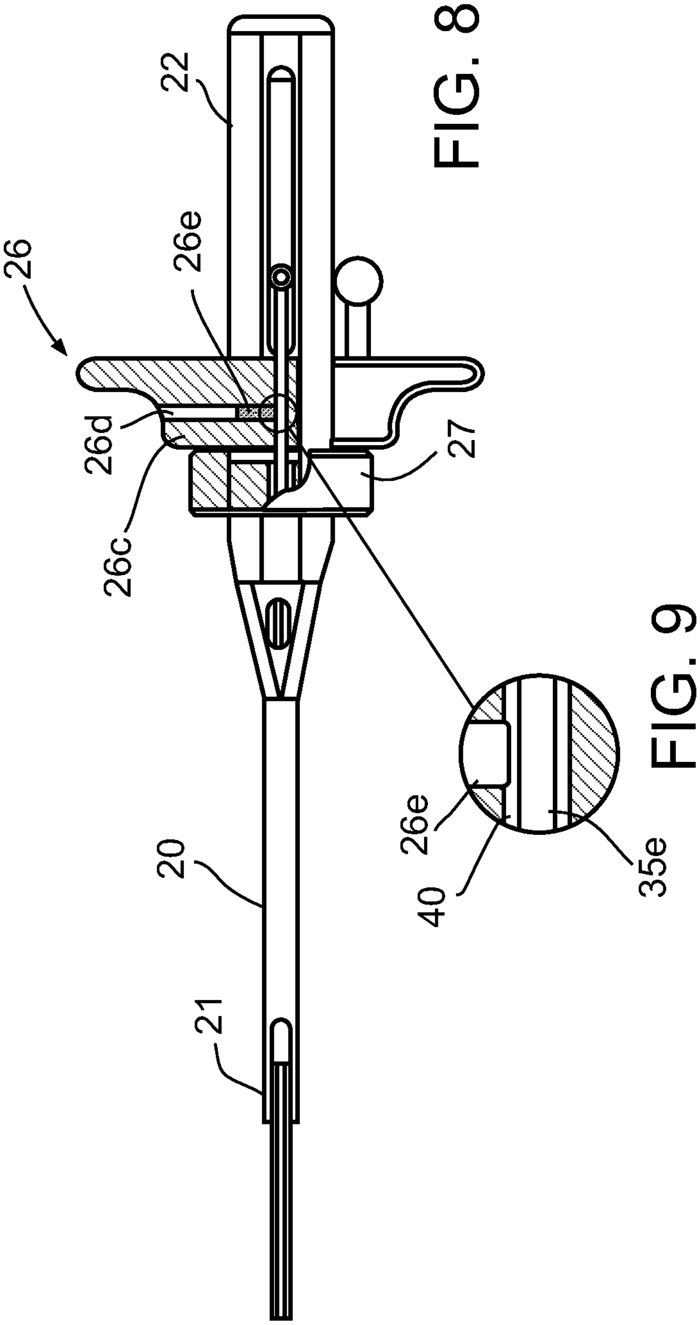
FIG. 8 is a sectional view along line VIII--VIII of FIG. 7.
FIG. 9 is an enlarged detail view of the encircled portion of FIG. 8.

The manner in which the hook 30 is coupled to manipulatable member 26, in the preferred embodiment, for moving the hook to its illustrated extended position or to its retracted position, is more particularly seen in FIGS. 8 and 9. As shown particularly in FIG. 8, the central pin 26*c* of manipulatable member 26 is formed with a bore 26*d* into which is threaded a screw 26*e* for securing manipulatable member 26 to an elongated sleeve 40 (FIG. 9) integrally formed with or fixed to the hook 30.

As shown in FIG. 5, and more particularly in FIGS. 2, 3 and 10A-10D, loop 35 is slidably received within hook 30. The two legs, 35*a*, 35*b* of the loop normally extend outwardly of the distal end of the hook and are joined at juncture 35*d* to a wire 35*e* passing through sleeve 40 of the hook. The proximal end of wire 35*e* is fixed to a connector 35*f* receiving the stem 28*a* of manipulatable member 28 (FIGS. 6A and 6B).

In an exemplary embodiment of the invention, the arrangement is such that hook 30 and loop 35 are normally in their extended positions as illustrated in FIG. 2, wherein the leg 34 of loop 30 is spaced away from the distal end 22 of handle 20, and loop 35 is extended outwardly of the hook leg 34. In this condition, in accordance with this embodiment, the hook 30 is inserted within bore $B_1$ (FIG. 1C) of the bone to which the suture is to be attached, with the loop 35 straddling bore $B_1$ and spaced away from the distal tip of leg 34 of the hook in order to receive one end of the suture to be attached to the bone. This arrangement enables the loop to be positioned for receiving the suture from bore B2 and not to collide with residues from drilling bore B2. In this embodiment, bore B2 is narrower than bore B1 thereby enabling the drill forming bore B2 to pass through the loop which is inserted through bore B1.

In another embodiment of the invention, hook 30 and loop 35 are in their retracted position, as shown in FIG. 5, when inserted into bore B1. The retracted position of hook 30 and loop 35 easies the insertion of the hook into the bore since the end of the hook is more rigid in its retracted position. Optionally, loop 35 is moved to its retracted position before forming bore B2 such that the drill forming bore B2 will pass through loop 35.

After the hook has thus been inserted into bore $B_1$ of the bone, in accordance with the above described embodiments, manipulatable member 26 is moved rearwardly and is locked in position for example by optional locking nut 27 to firmly clamp the hook to the bone, with the passageway 20*a* within handle 20 in alignment with bore $B_1$ and at a predetermined angle therewith (in this case 90°). A drill is then passed through passageway 20*a* of handle 20 to drill bore $B_2$ in the bone intersecting bore $B_1$ and extending slightly past that bore. After the drill is removed, the loop is moved to its extracted position if necessary. One end of the suture to be attached to the bone is then passed through passageway 20*a*, and between legs 35*a* and 35*b* of loop 35 to the end of bore $B_2$.

Knob 28 is then moved rearwardly to move loop 35 to its retracted position, i.e, towards the end hook leg 34, to firmly grasp the suture. The arrangement is such that the two bores $B_1$, $B_2$ are located for attaching the suture to the bone, one end of the suture may be extracted via bore $B_1$, and the other end of the suture may be extracted via bore $B_2$.

Figure 11:
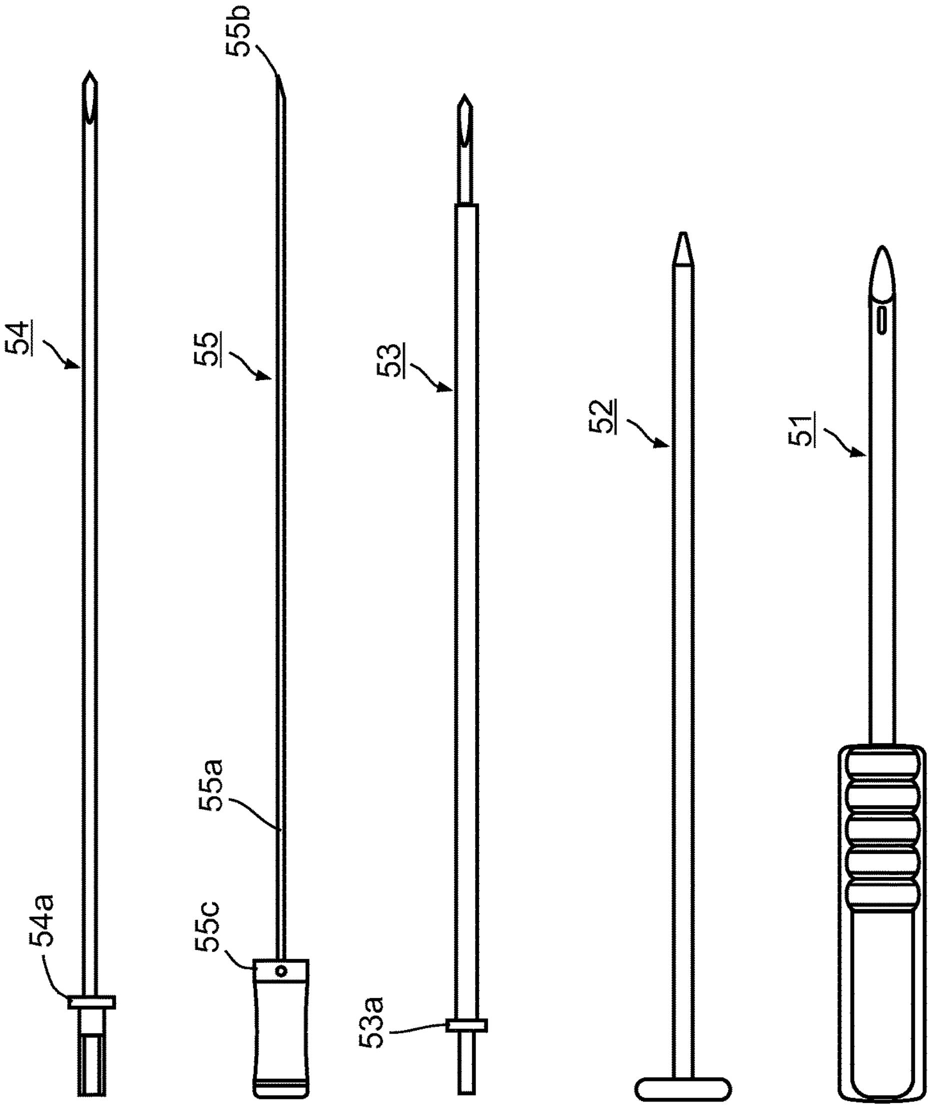
FIG. 11 illustrates the contents of a medical kit including the implement of FIG. 2, together with other implements, particularly useful for performing an arthroscopic surgical procedure according a preferred embodiment of the invention described herein.

The Medical Kit of FIG. 11

FIG. 11 illustrates the contents of a medical kit which may be supplied for use in performing the arthroscopic surgical procedure described above, and to include the medical implement as described above with respect to FIGS. 2-10D.

Such a kit would include one or more of the following additional tools: a drill guide 51, an obturator 52, and a drill bit 53, for use in forming bore $B_1$ (FIG. 1C) through the bone to which the suture is to be attached; a drill 54 for forming bore $B_2$ via passageway 20*a* of implement 50; and a suture loader 55 for forcing the suture, via passageway 20*a*, into bore $B_2$.

As shown particularly in FIG. 11, drill 54 used for forming bore $B_2$ includes a stop 54*a* at its proximal end to define the depth of bore $B_2$ to be produced thereby. The depth of bore B2 should be coordinated with the length of bore B1 and with the distance between distal end 22 of implement 50 and hook 30 after the implement is extended and clamped to the bone. This distance is varies for different bodies depending on the bone structure of the treated body. Optionally, stop 54*a* is not fixed and can be moved to vary the depth of bore B2 for different bones. In some embodiments, markings are provided on the extended portion of implement 50 to indicate the distance of extension. Drill 54 also includes markings which coordinate with the markings on implement 50 and allows positioning of stop 54*a* according to the distance between distal end 22 and hook 30 of implement 50. Alternatively, stop 54*a* is fixed and such that the depth of bore B2 will suit any bone in a body.

In an exemplary embodiment, drill 53 used for forming bore B1 also includes a stop 53*a*. In this embodiment, the position of stop 53*a* and stop 54*a* are coordinated so that the depth of bores B1 and B2 are defined and the bores intersect in the bone.

In an exemplary embodiment, drill 54 is narrower than drill 53 such that drill 54 will pass through a loop inserted in bore B1 which was formed by drill 53. Alternatively, drill 54 is used for forming both bore B1 and bore B2.

Figures 12, 13A, 13B, 14, 15:
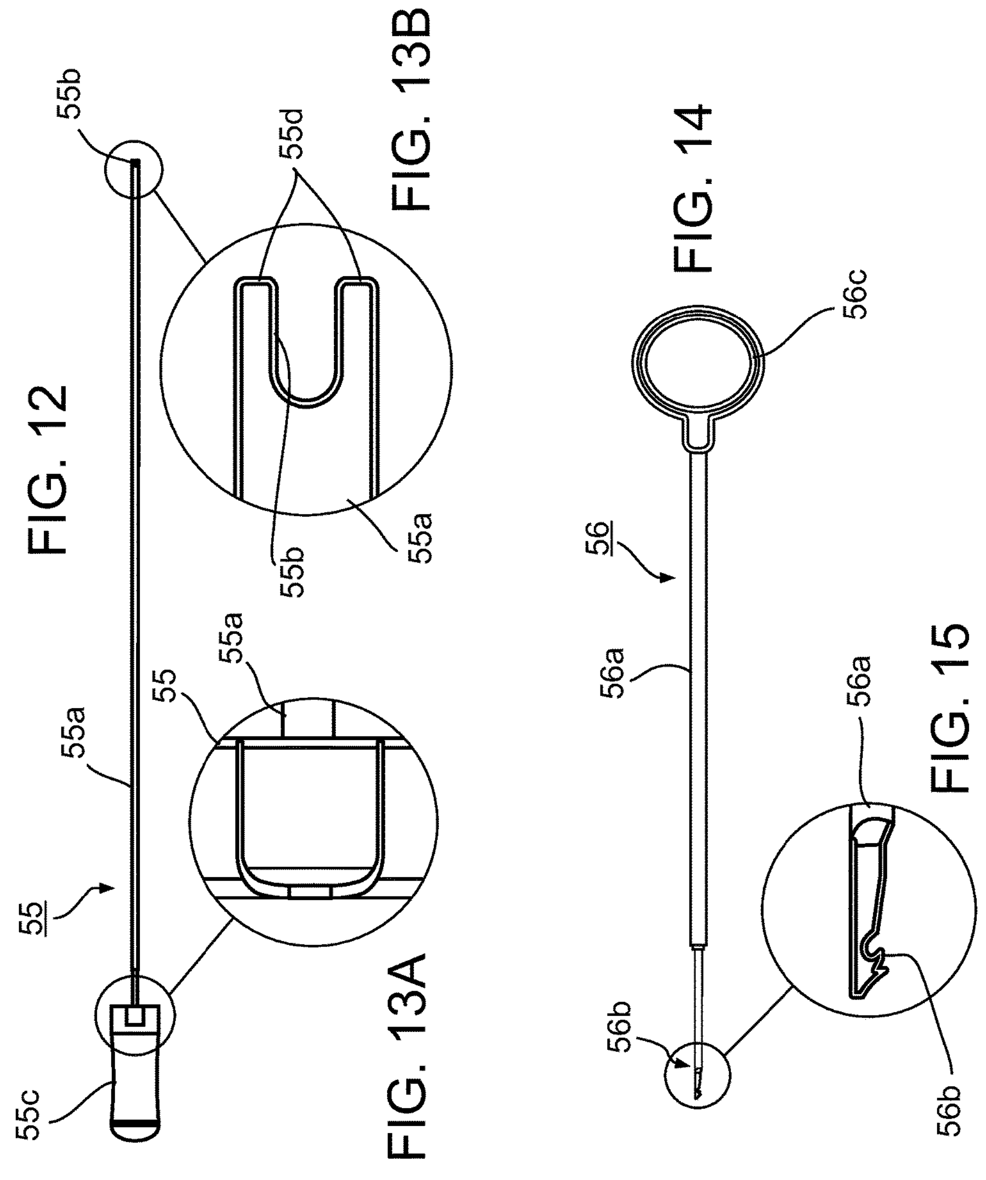
FIG. 12 more particularly illustrates the construction of the suture loading needle in the medical kit of FIG. 11.
FIGS. 13A and 13B are enlarged fragmentary views of the encircled portions of FIG. 12.
FIG. 14 illustrates a suture hook which may be included in the medical kit of FIG. 11 for use in performing the arthroscopic surgical procedure according to another embodiment of the invention.
FIG. 15 is an enlarged fragmentary view of the encircled portion of FIG. 14.
Figure 16:
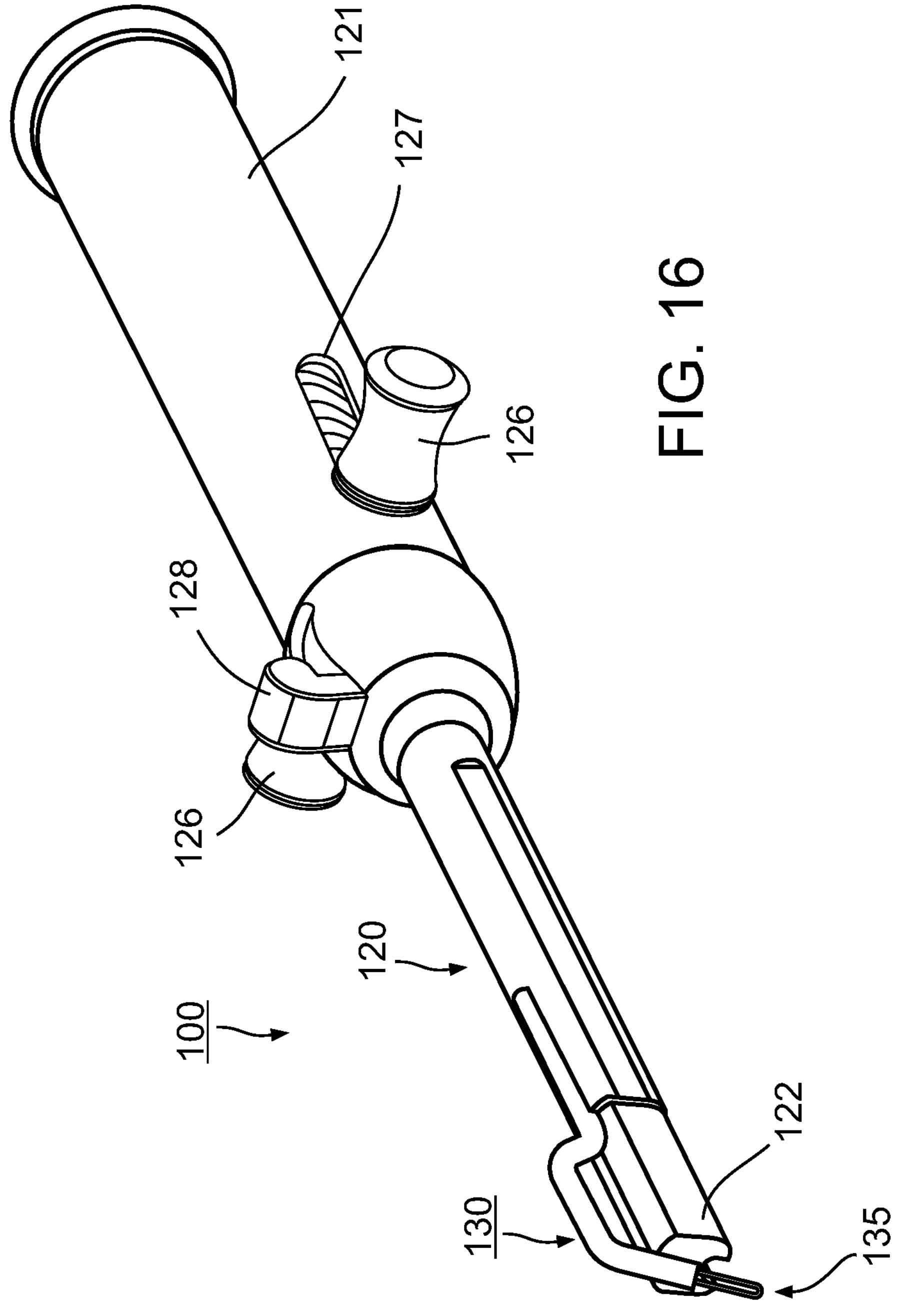
FIG. 16 is a perspective view of a second preferred embodiment of a medical bone-tunneling implement constructed according to the present invention for use in repairing a damaged shoulder joint.

In an exemplary embodiment, suture loader 55, as more particularly illustrated in FIGS. 12 and 13A-13B, includes a shank 55*a* formed with a notch 55*b* at its distal end and handle 55*c* at its proximal end, which shank is formed with a pair of opposed flat surfaces 55*d* parallel to notch 55*b*, to facilitate aligning the suture received within notch 55*b* to bore $B_1$ formed in the bone. Other designs of suture manipulators can also be used.

In an exemplary embodiment, cannulated drill guide 51 is inserted into passageway 20*a* of implement 50 and is adapted to receive both obturator 52 and drill 53. The obturator 52 is inserted within drill guide 51 in order to locate the exact location of bore $B_1$ and to clear a path through the soft tissue surrounding the bone for the drill to drill bore B1 in the bone. The obturator is then removed to enable drill 53 to drill bore $B_1$ via guide 51. After bore $B_1$ has been drilled, medical implement 50 is then used to drill bore $B_2$ by inserting hook 30 into bore $B_1$ to locate passageway 20*a* of implement 50 in precise alignment with bore $B_1$ and at a predetermined optimum angle thereto. In some situations an obturator may not be required.

Drill 54 is then passed through passageway 20*a* of implement 50 to drill bore $B_2$. Drill 54 is then removed and knob 28 is moved to extend loop 35 from hook 30, if it was not already extended during the drilling of bore $B_2$. The suture to be attached to the bone is then fed through passageway 20*a* by suture loader 55 traversing bore $B_1$ between the two legs 35*a*, 35*b* of loop 35 to the end of bore $B_2$. Optionally, drill 54 is cannulated and the suture is threaded through cannulated drill 54. In this option, the drill is removed after the thread is already in place or together with the entire implement. Loop 35 is then retracted within the end of hook 30 and to firmly clamp the suture to the end of hook 30. Hook 30 is removed from bore $B_1$ to expose the clamped end of the suture, and handle 20 of implement 50 is also removed to expose the other end of the suture. Accordingly, with the suture passing through the two bores $B_1$ and $B_2$, and the two ends of the suture exposed outwardly of these bores, the sutures may now be used for attaching the bone tendon to the bone, or for any other purpose, instead of the anchor pins as previously used.

It will thus be seen that the implement and kit described are particularly useful for arthroscopic medical procedures to attach a tendon to a bone, such as to repair a damaged shoulder joint. However, the invention could also be used in open surgical procedures, or for other procedures requiring the attachment of a suture to a bone instead of anchor pins heretofore used for such purposes.

Variation in Use of Medical Kit

FIGS. 14 and 15 illustrate a variation wherein one end of the suture is accessed and extracted via bore $B_1$, not by the loop 35 as described above, but rather by a suture hook, generally designated 56 in FIGS. 14 and 15. Such a suture hook includes a shank 56*a* formed with a crochet notch 56*b* at its distal end, and an optional handle 56*c* at its proximal end. Such a suture hook enables the end of the suture received within bore $B_2$ to be accessed and extracted via bore $B_1$, thereby obviating the need for the loop 35 in implement 50 as described above with respect to FIGS. 2-10D. Suture hook 56 illustrated in FIGS. 14 and 15 may thus also be included in the tool kit illustrated in FIG. 11 to be used instead of the loop 35 of implement 50.

The Medical Implement of FIGS. 16-21

FIGS. 16-21 illustrate another bone-tunneling implement constructed in accordance with an embodiment of the present invention, generally corresponding to the implement described above with respect to FIGS. 2-10D, but incorporating a number of modifications.

In the bone-tunneling implement illustrated in FIGS. 2-10D, the hook 30 is the movable element movable with respect to the distal end of the handle 20 in order to facilitate the reception of the hook into the first bore $B_1$, and for clamping the handle to the bone at a predetermined angle with respect to the first bore. In the medical implement of FIGS. 16-21 this arrangement in reversed; that is, in the medical implement of FIGS. 16-21, the movable member is the distal end of the handle, which is movable towards and away from the hook. Such an arrangement has the advantage of simplifying the mechanism for moving the movable element.

Another difference in the structure of the medical implement of FIGS. 16-21, over that of FIGS. 2-10D, is that the manipulatable member or knob 28 in FIGS. 2-10D is not slidable along an axis parallel to the longitudinal axis of the handle, but rather is pivotal along a pivot axis perpendicular to the longitudinal axis of the handle. In addition, the lock nut 27 used in the medical implement of FIGS. 2-10D to lock the manually-manipulatable member 26, is omitted. Such features not only simplify the structure, but also facilitate its use by the surgeon.

The medical implement illustrated in FIGS. 16-21 is generally designated 100. It includes a handle 120 having a proximal end 121 for manual grasping, and a distal end 122 for engagement with a bone in which a suture is to be attached. As in the previously-described embodiment, the bone would be pre-formed with a first bore $B_1$ (FIG. 1C). The medical implement of FIGS. 16-21 also includes a hook 130 at the distal end of the handle, and a loop 135 movable to an extended position with respect to the hook for facilitating entry of one end of the suture through the loop, and to a retracted position for clamping the respective end of the suture, as described above with respect to FIGS. 2-10D.

In the implement of FIGS. 2-10D, the hook (30) is the movable element with respect to the distal end (22) of the handle; the construction of FIGS. 16-21 reverses these parts.

That is, in the construction of FIGS. 16-21, the hook 130 is fixed, and the distal end 122 of the handle is movable towards and away from the hook in order to facilitate the entry and removal of the hook into the first bore $B_1$.

Figures 17, 18, 19, 20, 21:
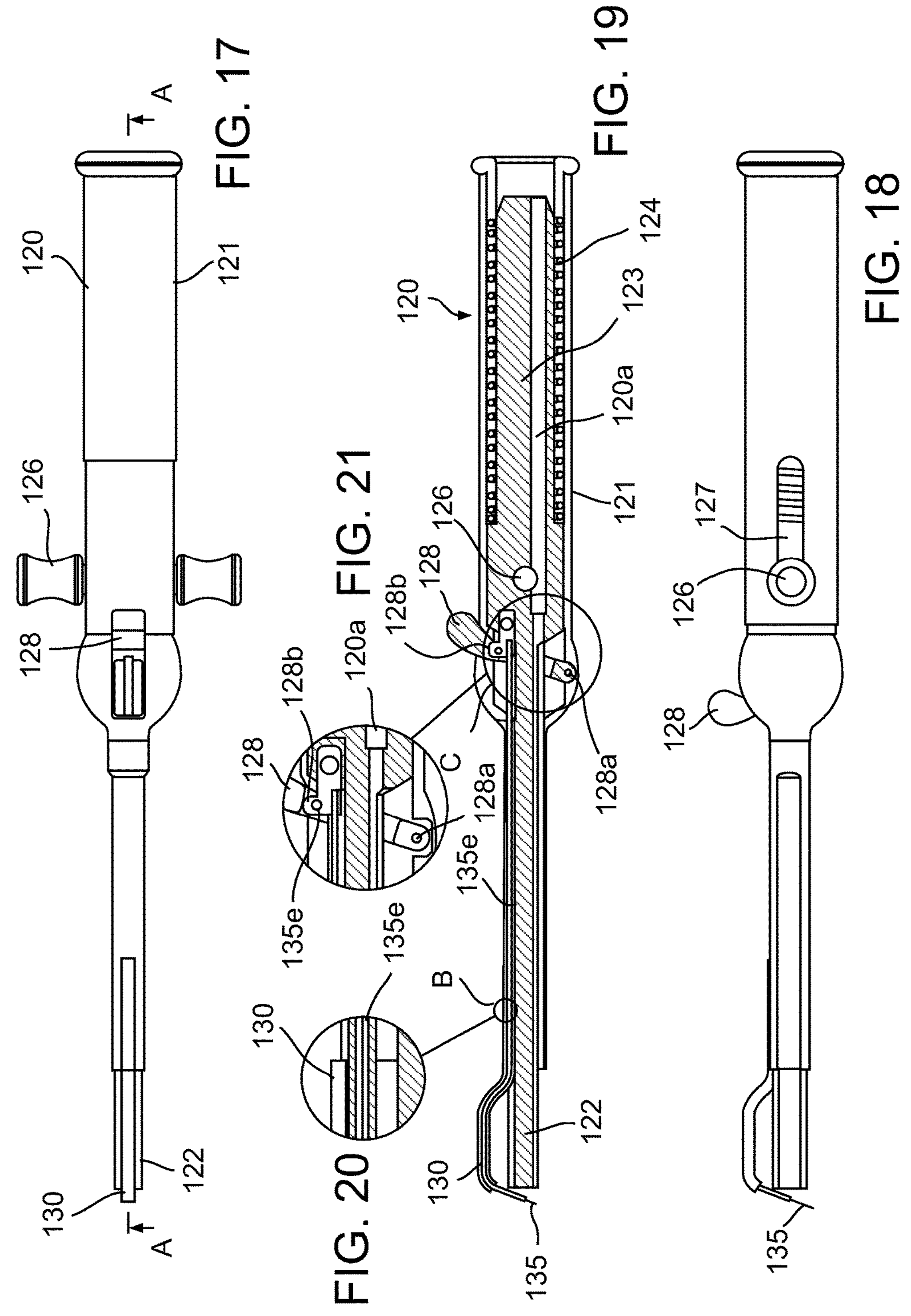
FIGS. 17 and 18 are top and side views, respectively, of the medical implement of FIG. 16.
FIG. 19 is a longitudinal sectional view along section line A--A of FIG. 17.
FIG. 20 is an enlarged fragmentary view of encircled portion B of FIG. 19.
FIG. 21 is an enlarged fragmentary view of the encircled portion C of FIG. 19.

This feature can be best seen in FIG. 19, wherein it will be seen that the handle 120 is hollow, and slidably receives a core 123 having a distal end 122 movable towards and away from the hook 130.

As clearly seen in FIG. 19, core 123 is urged by a spring 124 in the direction of bringing the distal end 122 into engagement with the hook 130, but may be manually moved rearwardly by means of manipulatable member 126 having a stem passing through longitudinal slots 127 (FIG. 18) in handle 120 so as to permit the distal end 122 to be retracted rearwardly of hook 130 against the bias of spring 124. As further seen particularly in FIG. 19, the core 123 is formed with passageway 120*a* (corresponding to passageway 20*a* in FIGS. 2-10D) used for making a second bore $B_2$ shown in FIG. 1C. At the distal end 122, passageway 120*a* is a slot in core 123.

Loop 135 received within hook 130 is basically of the same construction as described above with respect to loop 35 in FIGS. 2-10D, in that it is coupled to knob 128 to move the hook to its extended and retracted positions in order to grasp a suture passed between the two legs of the hook for extraction from bore $B_1$, as described above with respect to FIGS. 2-10D. The coupling of the loop 135 to knob 128 is also effected by means a wire 135*e* passing through the distal end of handle 120.

In the implement of FIGS. 16-21, however, manipulatable knob 128 for loop 135 is pivotal about an axis 128*a* extending perpendicularly to the longitudinal axis of the handle 120 and located slightly above that longitudinal axis, as can be seen particularly in FIG. 19. Thus, as shown in FIG. 19, loop 135 would normally be urged, by spring 124 to its retracted position within hook 130 (FIG. 19), but is conveniently movable to its extended position, shown in FIG. 18, by merely pivoting knob 128 forwardly, whenever it is desired to extend the loop for receiving the end of the suture. Releasing the knob will then effect the retraction of the loop to firmly grasp the suture, as described above with respect to the implement of FIGS. 2-10D.

In addition, whereas hook 30 shown in FIG. 2 formed an angle of about 90° between horizontal section 33 and end section 34, in the embodiment shown in FIGS. 16-21, hook 130 forms a larger angle of about 110°-115° between horizontal section 33 and end section 34. Accordingly, with this embodiment, the angle between bores B1 and B2 formed using implement 100 is about 65°-70°.

In substantially all other respects, the bone-tunneling implement illustrated in FIGS. 16-21 is constructed, and operates, in the same manner as described above.

It is to be understood that, where applicable, implements according to various embodiments of the invention can include features taken from both described embodiments of the bone-tunneling implements. Furthermore, it should be clear that other methodologies to provide the functions performed by the two above embodiments can also be used.

Method of Attaching a Suture to a Bone (FIGS. 22 and 23A-G)

Figure 22:
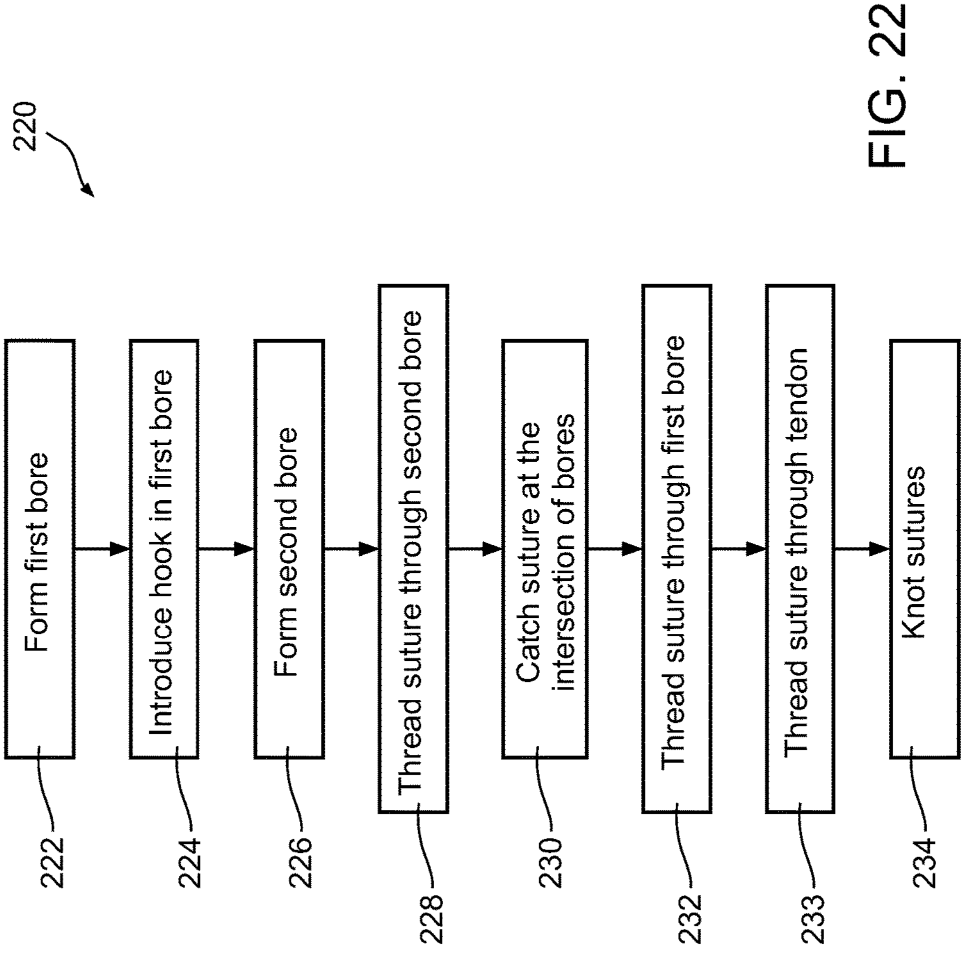
FIG. 22 is a flow diagram of a method of attaching a suture to a bone in accordance with an exemplary embodiment of the invention.

FIG. 22 is a block diagram of a method 220 of attaching a suture to a bone in accordance with an exemplary embodiment of the invention. FIGS. 23A-G are illustrations of stages of method 220. the illustrations and description below refers to implement 100 shown in FIGS. 16-21. It is noted that method 220 with appropriate changes may be applied with implement 50 shown in FIGS. 2-10D or other variations of the implement.

Figures 23A, 23B, 23C, 23D:
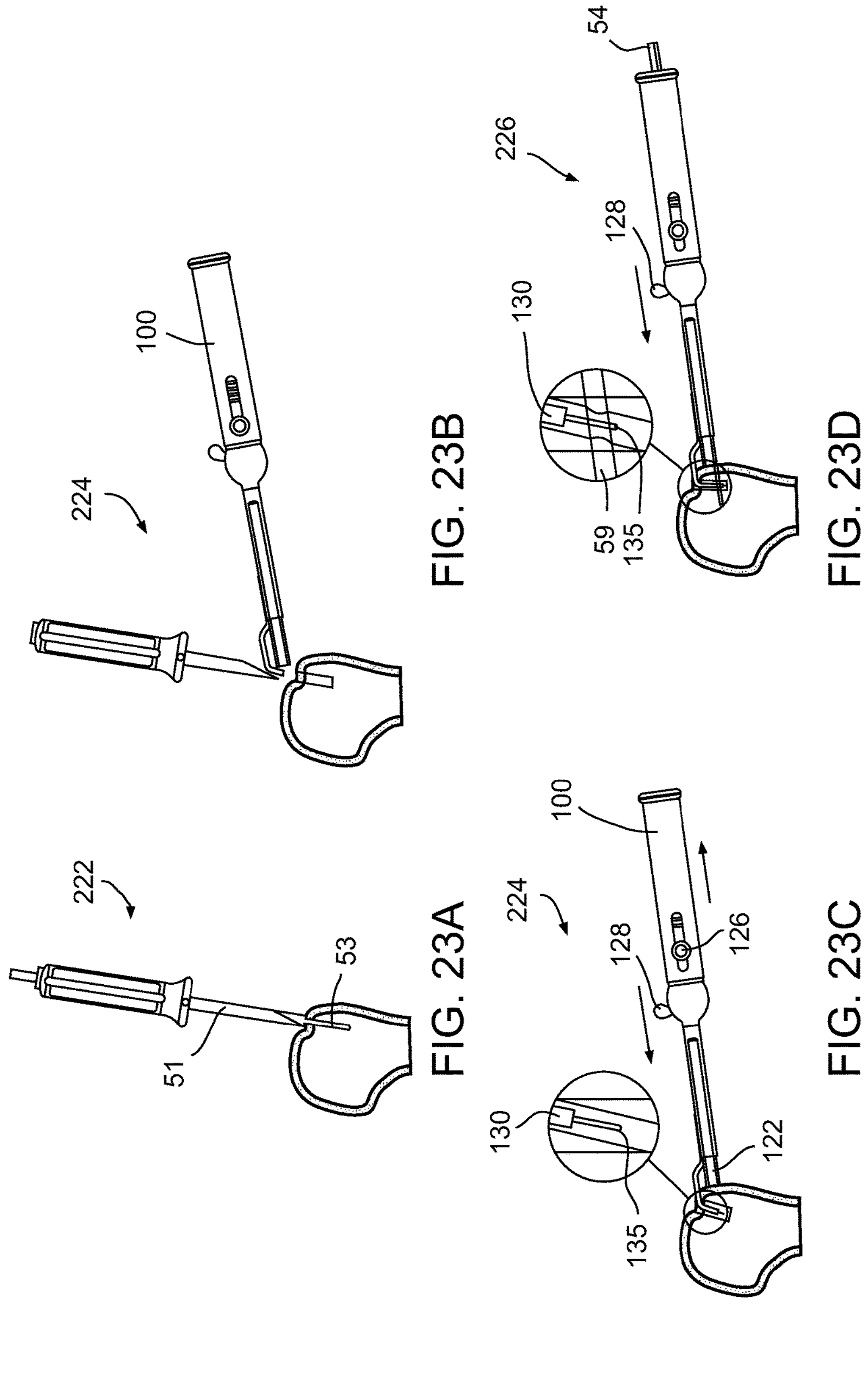
FIGS. 23A-J are schematic illustrations of phases of the method of FIG. 22.

A first bore B1 is formed in the humerus bone at 222. Preferably, bore B1 is formed near the greater tubercle 6 shown in FIG. 23A and FIGS. 1A-1C and is not long enough to exit the bone. Optionally, as shown in FIG. 23A, bore B1 is drilled with a drill bit 53 inserted through drill guide 51. Optionally, an obturator is first inserted through drill guide 51 in order to clear a path through the soft tissue surrounding the bone. Alternatively, bore B1 is formed by any other method known in the art.

Hook 130 is then inserted into bore B1 at 224. Optionally, the hook is inserted through drill guide 51, as indicated in FIG. 23B, in order to ease locating bore B1 and the drill guide is removed after insertion.

Optionally, the insertion of the hook into bore B1 is used as a reference point for forming bore B2, such that bores B1 and B2 intersect at a predetermined angle. Alternatively or additionally, hook 130 is used as an arm clamping implement 100 to the bone. Before inserting hook 130 to bore B1, manipulatable member 126 is moved rearwardly so as permit distal end 122 of the core to be retracted rearwardly of hook 130. After insertion of hook 130 in bore B1, manipulatable member 126 is released and distal end 122 is clamped to the bone by bias of spring 124 as shown in FIG. 19, or otherwise.

FIG. 23C depicts the hook inserted into the first hole and distal end 122 clamped to the bone. As further shown in FIG. 23C, manipulatable knob 128 is moved to shift loop 135 to its extended position.

At 226 a second bore B2 is formed through the bone (FIG. 23D) at a predetermined angle from bore B1. Bore B2 is drilled to a depth such that bore B2 meets bore B1 in the humerus bone thereby enabling a suture to be threaded through the two bores. Preferably, bores B1 and B2 extend past the intersection of the bores in the bone such that drill 54 passes through loop 135 in bore B1. Preferably, bore B2 is not long enough to exit the bone. Optionally, bores B1 and B2 define a 70° angle in the bone. Preferably, bores B1 and B2 define an angle of between 65° and 75° in the bone.

Optionally, before drilling bore B2, an obturator, such as the obturator 52 shown in FIG. 11, is used to clear the path and locate the exact location of bore B2. Bore B2 is then drilled at the location indicated by the obturator, using a drill such as drill 54 shown in FIG. 11.

Figure 23E:
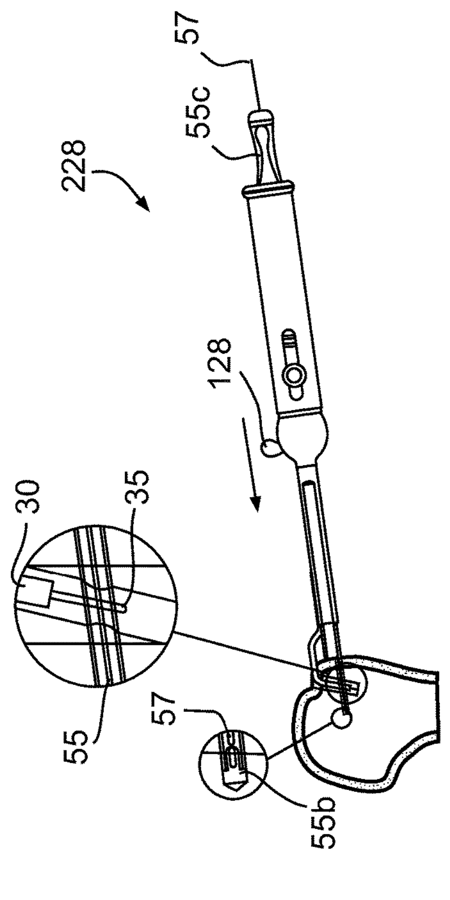
Figure 23F:
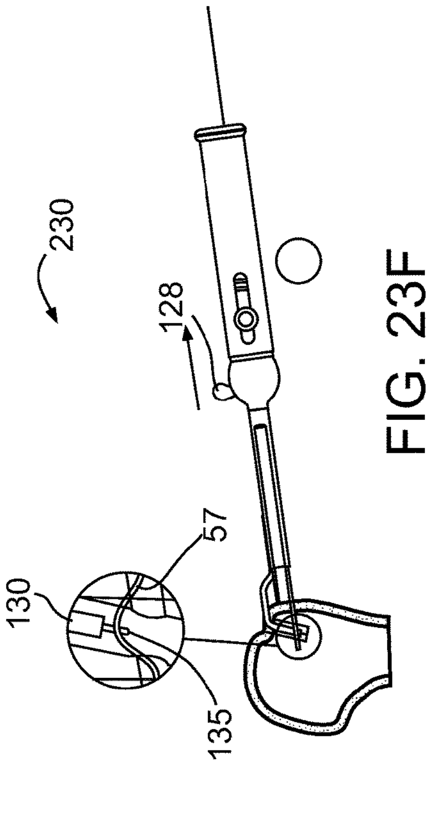
Figure 23G:
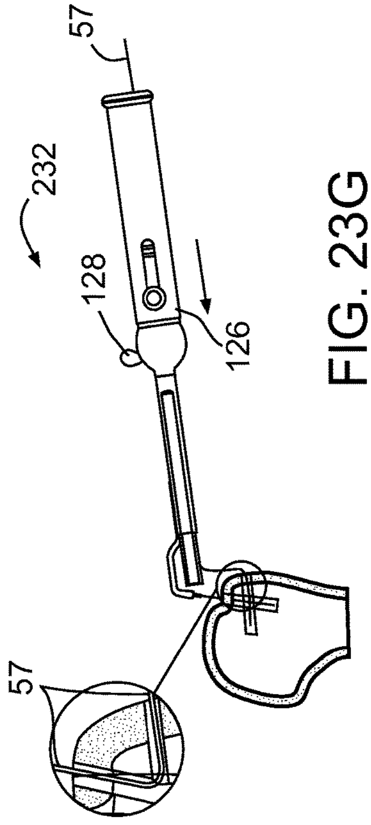

After forming bore B2 a first end of a suture 57 is threaded through bore B2 at 228. As shown in FIG. 23E, a suture loader such as suture loader 55 depicted in FIG. 12 is optionally used for threading suture 57 through bore B2 and through loop 135 extending from hook 130. Suture loader 55 is then removed, leaving suture 57 in the bore.

At 230 the first end of the suture is caught at the intersection of bores B2 and B1 by loop 135. Manipulatable knob 128 is moved to shift loop 135 to its retracted position inside hook 130. Suture 57 which was threaded through loop 135 is now caught inside hook 130.

At 232 manipulatable member 126 is moved to release distal end 122 from being clamped to the bone. Hook 130 is removed from bore B1 and suture 57 which is clamped in hook 130 is thereby threaded through bore B1. The end of the suture is then extracted from the bone by threading through bore B1 at 232. As shown in the magnified section of FIG. 23G, suture 57 is now threaded through a channel in the bone consisting of bores B1 and B2.

In an alternative embodiment, the suture is first threaded into bore B1 and caught through bore B2.

At 233 the suture is threaded through the tendon according to any procedure known in the art. The tendon is then pulled into place by means known in the art. At 234 the two ends of the suture, the first end extending from bore B1 and the second end extending from bore B2 and tendon 10 may be knotted together thereby attaching the tendon to the humerus bone. FIG. 23H is a coronal section view of a humerus bone illustrating a suture knotted through the bone and tendon. The suture, threaded through a into bore B1 is exited bore B2 at b, retrieved through tendon 10 at c and is knotted at d. FIG. 23I is a lateral view of a row of sutures tied over tendon 10 in accordance with an exemplary embodiment of the invention. A first suture is passed through the bone at a1 to b1 and retrieved through the tendon at c1 and then knotted at d1. A second suture is passed through a channel in the bone from a2 to b2 and passed through the tendon at c2 to be knotted at d2, etc.

Figure 23J:
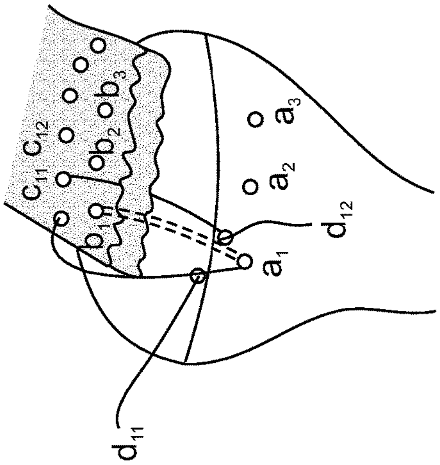
Figure 23I:
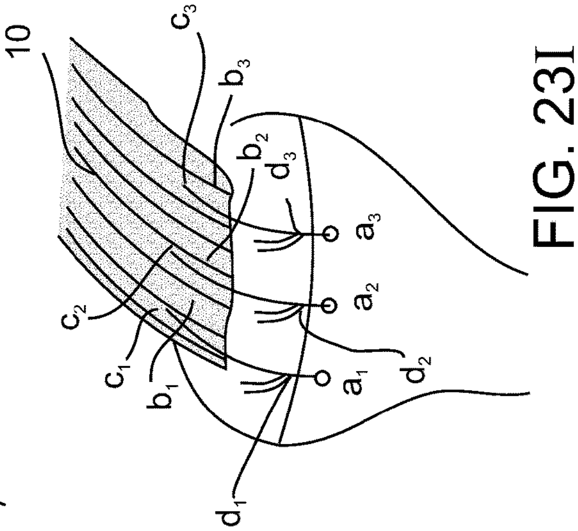
Figure 23H:
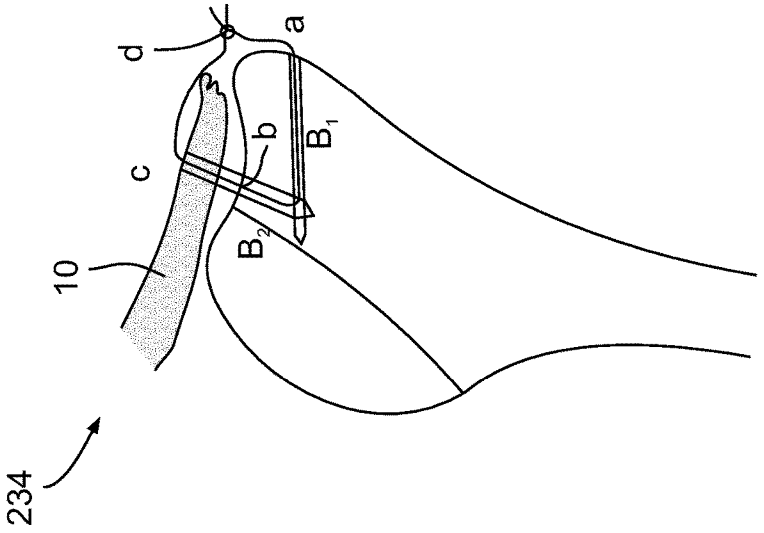

FIG. 23J illustrates a lateral view of another embodiment of the invention where two sutures are passed through a single bone channel and are tied over different locations through the tendon. For example, a first and a second suture are threaded through a bone channel from a1 to b1. The first suture is retrieved through the tendon at c11 and knotted at d11. The second suture is retrieved through the tendon at c12 and knotted at d12.

It is noted that a plurality of ways of tying the sutures are known in the art. FIGS. 23I-J are provided an example and other methods such as for example crossing the sutures over the tissue, to increase the area of the tendon held against the bone, are also covered by the present invention.

Figure 24:
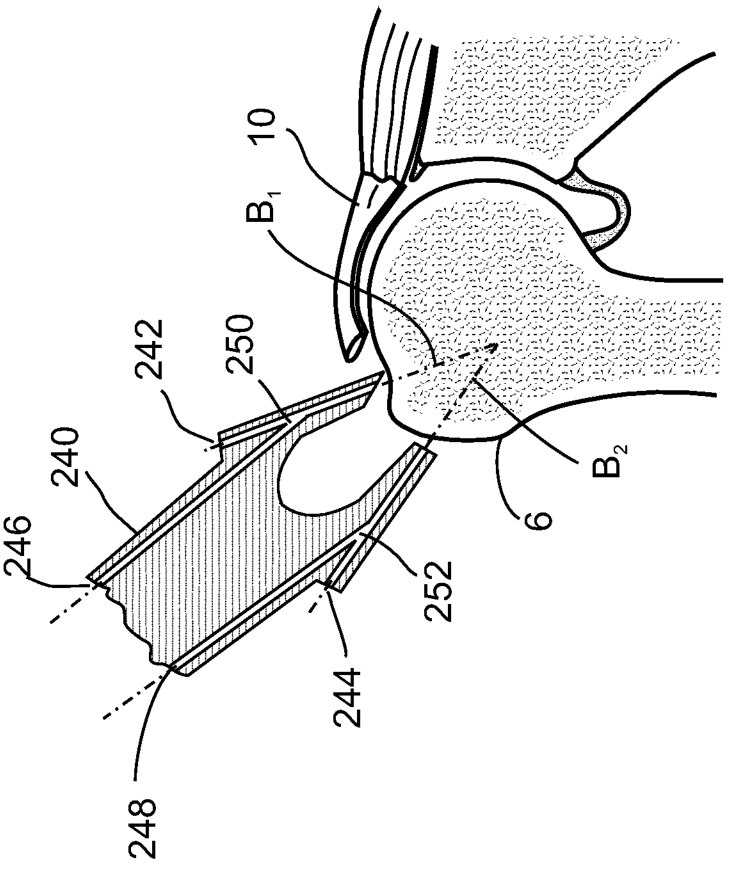
FIG. 24 is a schematic illustration of an implement used for repairing a damaged shoulder joint in accordance with another exemplary embodiment of the invention.

The Medical Implement of FIG. 24

In another embodiment of the invention, bores B1 and B2 are formed with a same implement 240 as shown in FIG. 24.

Implement 240 includes two channels 242 and 244 for receiving tools such as drills, holders, etc. Instrument 240 is brought close to the bone at the greater tubercle 6. A drill, such as drill 53 shown in FIG. 11, is inserted into channel 242 for forming a first bore B1. Optionally, an obturator, such as obturator 52 shown in FIG. 11, is first inserted into channel 242 for clearing the path through the soft tissue and indicating the location of bore B1.

A pin or hook is then inserted into channel 242 and bore B1 for positioning implement 240 to the bone in order to stabilize the implement when forming a second bore B2. optionally, the drill used for forming bore B1 is kept in the bore for stabilization of implement 240 and a second drill is used for forming bore B2.

A drill is then inserted through channel 244 and second bore B2 is formed. Channels 242 and 244 are located in implement 240 such that bores B1 and B2 formed with drills inserted through the channels, intersect in the bone. Preferably, bores B1 and B2 are not long enough to exit the bone. Optionally, a stop on the drill forming bores B1 and B2 causes the bores to be formed to a certain depth such that the bores will intersect in the bone and will not cross the bone.

In the embodiment shown in FIG. 24, the angles formed between the bores is preferable less than 90° so as to allow the two bores to be formed from the same side of the bone. Optionally, the bores define an angle of less than 45° in the bone. Optionally, the bores define an angle of less than 30° in the bone.

Implement 240 further comprises two channels 246 and 248 for receiving a suture. Channels 246 and 248 join with channels 242 and 248 at intersection points 250 and 252 respectively. After bores B1 and B2 are formed, a suture is inserted through channel 246 and bore B1 and is retrieved through bore B2 and channel 248 in a manner similar to that described with respect to the embodiments shown in FIGS. 2 and 16 above.

It will be appreciated that other variations, modifications and applications of the invention may be made. For example, other means may be used for extracting the end of the suture via bore $B_1$ than those described above. In addition, other constructions of the slidable manipulatable members 26 and 28 may be used for removing the hook and/or the loop. The couplings of manual manipulatable member 26 may include a slip or yielding coupling in order to prevent excessive force from being applied by hook 30 to the bone, and thereby reduce the possibility of breakage of the bone.

Many other variations, modifications and applications of the invention will be apparent.

The invention claimed is:

1. A medical implement for attaching a suture to a bone, comprising:

a handle having a proximal end for manual grasping and a distal end for engagement with said bone to which said suture is to be attached, said bone being preformed with a first bore, said handle extending axially from said proximal end to said distal end;

a hook extending from the distal end of the handle and configured for reception in said first bore of the bone;

a movable member resiliently coupled to said handle and urged in an axial direction of the handle toward the hook responsive to the resilient coupling, said movable member being movable to a retracted position with respect to the hook to facilitate reception of the hook into said first bore, and biased to an extended position with respect to the proximal end of the handle for clamping said handle to said bone with a resilient force at a predetermined angle with respect to said first bore;

and a manually manipulatable member coupled to said movable member for moving said movable member to said extended and retracted positions;

said handle being formed with a passageway extending longitudinally therethrough from its proximal end to its distal end, said passageway being configured for receiving a drill, for drilling a second bore through said bone at said predetermined angle with respect to said first bore and for passing through the passageway one end of a suture to traverse, and to extend past, said first bore such that said one end of the suture is accessible through said first bore for being pulled out therefrom, while the opposite end of the suture is accessible through said second bore for pulling out therefrom in order to attach the suture to said bone.

2. The implement according to claim 1, wherein said movable member is in said distal end of the handle.

3. The implement according to claim 1, wherein said hook includes a loop movable to an extended position with respect to the hook for facilitating entry of said first end of the suture through said loop into said first bore of the bone, and to a retracted position towards said hook for clamping said first end of the suture to enable pulling out said first end of the suture through said first bore of the bone;

and wherein said handle includes a second manually manipulatable member coupled to said loop for moving the loop to its extended and retracted positions.

4. The implement according to claim 3, wherein said second manipulatable member includes a knob coupled to a stem slidable through a slot in said handle and coupled to said loop.

5. The implement according to claim 4, wherein said stem is coupled to said loop by a cable extending through a sleeve in said handle coupled to said hook.

6. The implement according to claim 4, wherein said knob is slidable along an axis parallel to a longitudinal axis of the handle.

7. The implement according to claim 4, wherein said knob is pivotable along a pivot axis perpendicular to a longitudinal axis of the handle.

8. The implement according to claim 1, wherein said predetermined angle is about 70°.

9. The implement according to claim 1, wherein said manually manipulatable member is a slidable member slidably received on the proximal end of said handle.

10. The implement according to claim 9, wherein said proximal end of the handle includes a threaded section, and further includes a nut threaded on said threaded section to lock said slidable member in position.

11. The implement according to claim 9, wherein said slidable member is coupled to said hook by an elongated member extending through said handle.

12. The implement according to claim 11, wherein said slidable member includes a pair of transversely-aligned finger pieces, and a central stem affixed to said elongated member and slidable within a slot formed in said handle.

13. The implement according to claim 12, wherein said elongated member is an elongated sleeve fixed to said hook.

14. The implement according to claim 1, wherein said first and second bores are linear bores.

15. A medical kit for attaching a suture to a bone in an arthroscopic surgical procedure, comprising:

the medical implement according to claim 1;

and a drill receivable within said passageway of the handle for drilling said second bore in the bone;

said drill including a stop engageable with said proximal end of the handle to fix a length of the second bore to extend past said first bore, to thereby permit said one end of the suture to traverse and extend past said first bore in order to facilitate its access and extraction via said first bore.

16. The kit according to claim 15, wherein said drill has a diameter of 2.5 mm.

17. The kit according to claim 15, wherein said kit further includes a suture loader sized and configured for reception in said passageway of the handle and for passing said suture through said second bore past said first bore in the bone.

18. The kit according to claim 17, wherein said suture loader includes a distal end formed with a slot for receiving said suture, and a proximal end formed with a handle having flat opposed sides parallel to said slot for orienting the suture loader with respect to the suture to be received within said slot.

19. The kit according to claim 15, wherein said kit further includes:

a drill guide having a distal end engageable with said bone at the location of the first bore to be formed therein; and a proximal end opposite to said distal end;

and a second drill receivable within said drill guide, said second drill including a distal end formed with cutting edges to drill said first bore in the bone, and a proximal end formed with a shoulder engageable with the proximal end of the drill guide for defining a depth of the first bore to be drilled by said second drill.

20. The kit according to claim 19, wherein said second drill has a diameter of 2.9 mm.

21. The kit according to claim 15, wherein said kit further includes a suture hook sized and configured for reception in said first bore and for extracting said one end of the suture therethrough.

22. An implement according to claim 1, wherein the handle is elongate and wherein said hook extends from the handle in a direction of an axis of the elongate handle.

23. An implement according to claim 1, wherein said movable member is configured for clamping the passageway against the bone when the hook is inserted into the first hole.

24. The implement according to claim 1, wherein the manually manipulatable member is the only member of the implement that requires manual manipulation for both reception of the hook into said first bore and for clamping said handle to said bone.

25. A medical implement, comprising:

a hook that is formed from a single piece with a bend to hook a first bore in a bone;

a passageway for placement at an entrance to a second bore in the bone; and a grasper extending from the hook, said grasper being adapted to grasp an end of a suture inserted through the passageway and through the second bore, wherein said passageway is movable by retraction or extension of a resilient member towards and away from said hook.

26. The implement according to claim 25, wherein said grasper is adapted to grasp a first end of said suture inserted through the passageway and through the second bore, while the second end of the suture is left outside the second bore in the bone.

27. The implement according to claim 25, wherein said grasper comprises a loop.

28. The implement according to claim 25, wherein said first and second bores are linear bores.

29. A medical implement according to claim 25, wherein the hook is formed from a first section and a second end section, the bend being between the first and second sections, and wherein the first section is substantially parallel to said passageway and the second end section is substantially perpendicular to said first section.

30. A medical implement according to claim 29, wherein the second end section is sized and shaped so that the second end section may be received in its entirety in a bore thereby causing the first section to at least partially rest on the bone.

31. A medical implement comprising:

an elongate element comprising a proximal end for manual grasping and a distal end for engagement with a bone;

a first passageway formed in the elongate element and extending from said proximal end to said distal end of the elongate element; and a hook formed in said distal end of the elongate element capable of slidably inserting into a straight bore in the bone, wherein at least one of the hook and a part of the elongate element formed with the first passage way is movable by retraction or extension of a resilient member from a retracted position to an extended position along or parallel to an axis of said elongate element and wherein the hook, the part of the elongate element and the resilient member provide for clamping the bone with a resilient force, wherein the resilient member is urged in an axial direction of the elongate element toward the distal end of the elongate element responsive to the resilient member.

32. A medical implement according to claim 31, wherein the hook comprises a second passageway including a grasper movable to an extended position with respect to the second passageway where the grasper extends from the second passageway and to a retracted position where the grasper is entirely positioned inside the second passageway.

33. An implement according to claim 32, wherein the grasper is permanently coupled to said second passageway.

34. An implement according to claim 31, wherein said hook is formed from a first section and a second end section, and wherein the second end section is substantially perpendicular to said first section.

35. An implement according to claim 34, wherein said first section is substantially parallel to the axis of the elongate element.

* * * * *